US007867548B2

(12) United States Patent
Otis et al.

(10) Patent No.: US 7,867,548 B2
(45) Date of Patent: Jan. 11, 2011

(54) THERMAL EJECTION OF SOLUTION HAVING SOLUTE ONTO DEVICE MEDIUM

(75) Inventors: David Otis, Corvallis, OR (US); Jeffrey A Nielsen, Corvallis, OR (US); Wayne E Gisel, Philomath, OR (US); Gerald F Meehan, Corvallis, OR (US); David Leigh, Corvallis, OR (US); Isaac Farr, Corvallis, OR (US); NK Peter Samuel, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1111 days.

(21) Appl. No.: 11/553,834

(22) Filed: Oct. 27, 2006

(65) Prior Publication Data

US 2008/0100685 A1 May 1, 2008

(51) Int. Cl.
*A61L 33/00* (2006.01)

(52) U.S. Cl. ...................... 427/2.1; 427/2.24; 427/2.25; 427/421.1; 427/422; 427/424; 427/425; 427/427.2; 427/427.3; 427/427.4; 427/427.5; 358/447; 347/23; 424/93.21; 378/143; 623/1.11; 606/198; 101/35

(58) Field of Classification Search ................ 427/2.24; 358/447; 347/23; 424/93.21; 378/143
See application file for complete search history.

(56) References Cited

U.S. PATENT DOCUMENTS 4,069,084 A 1/1978 Miodozeniec et al.
4,197,289 A 4/1980 Sturzenegger et al.
4,322,449 A 3/1982 Voss et al.
4,349,529 A 9/1982 Morcos et al.
4,548,825 A 10/1985 Voss et al.
4,905,589 A 3/1990 Ackley
5,025,325 A * 6/1991 Hudson ...................... 358/447
5,609,908 A 3/1997 Voss
5,714,007 A 2/1998 Pletcher et al.
5,881,716 A 3/1999 Wirch et al.
5,925,732 A 7/1999 Ecker et al.
6,086,942 A 7/2000 Carden, Jr. et al.
6,143,353 A 11/2000 Oshlack et al.
6,395,326 B1 5/2002 Castro et al.
6,645,547 B1 11/2003 Shekalim et al.
6,692,738 B2 * 2/2004 MacLaughlin et al. ... 424/93.21
2001/0016177 A1 8/2001 Pelc et al.
2002/0149641 A1 * 10/2002 Du et al. ........................ 347/23
2003/0223546 A1 * 12/2003 McGregor et al. .......... 378/143
2006/0217801 A1 9/2006 Rosenthal

FOREIGN PATENT DOCUMENTS

EP 0369445 A1 5/1990
JP 10016208 A * 4/1998
WO 03005950 A2 1/2003
WO 2004026182 A2 4/2004
WO 2006-102524 A 9/2006
WO WO 2006/102524 * 9/2006

* cited by examiner

*Primary Examiner*—Michael Barr
*Assistant Examiner*—Andrew Bowman

(57) ABSTRACT

A solution is provided that includes a non-aqueous organic solvent within which a solute has been dissolved. A thermal-fluid ejection mechanism is provided that has fluid-ejection nozzles and that is capable of thermally ejecting the solution. A device medium is provided that has a three-dimensional surface on which the solution is to be ejected. The fluid-ejection nozzles of the thermal fluid-ejection mechanism are controlled to eject the solution onto the three-dimensional surface of the device medium in accordance with a desired pattern.

17 Claims, 16 Drawing Sheets

| | PASS 1 | PASS 2 | PASS 3 | PASS 4 |
|---|---|---|---|---|
| 100% | YES | YES | YES | YES |
| 50% | YES | NO | YES | NO |
| 25% | YES | NO | NO | NO |

920

THERMAL EJECTION OF SOLUTION HAVING SOLUTE ONTO DEVICE MEDIUM

BACKGROUND

Many types of medical devices have drugs coated on them prior to their being implanted or inserted into people. Such medical devices include stents, heart implants, and needles, as well as other types of medical devices. Current approaches for coating drugs onto medical devices include dip coating, ultrasonic spray coating, brushing, as well as piezoelectric fluid ejection, among other types of approaches.

All of these approaches, however, are disadvantageous to some degree. Dip coating and ultrasonic spray coating lack precision in both placement and quantity applied. Brushing is tedious, and also lacks precision. Piezoelectric fluid ejection of drugs is usually achieved by using a single piezoelectric fluid-ejection nozzle, which can mean that coating takes a relatively long time, since the entire coating is ejected from a single nozzle.

DETAILED DESCRIPTION

Overview

Figure 1:
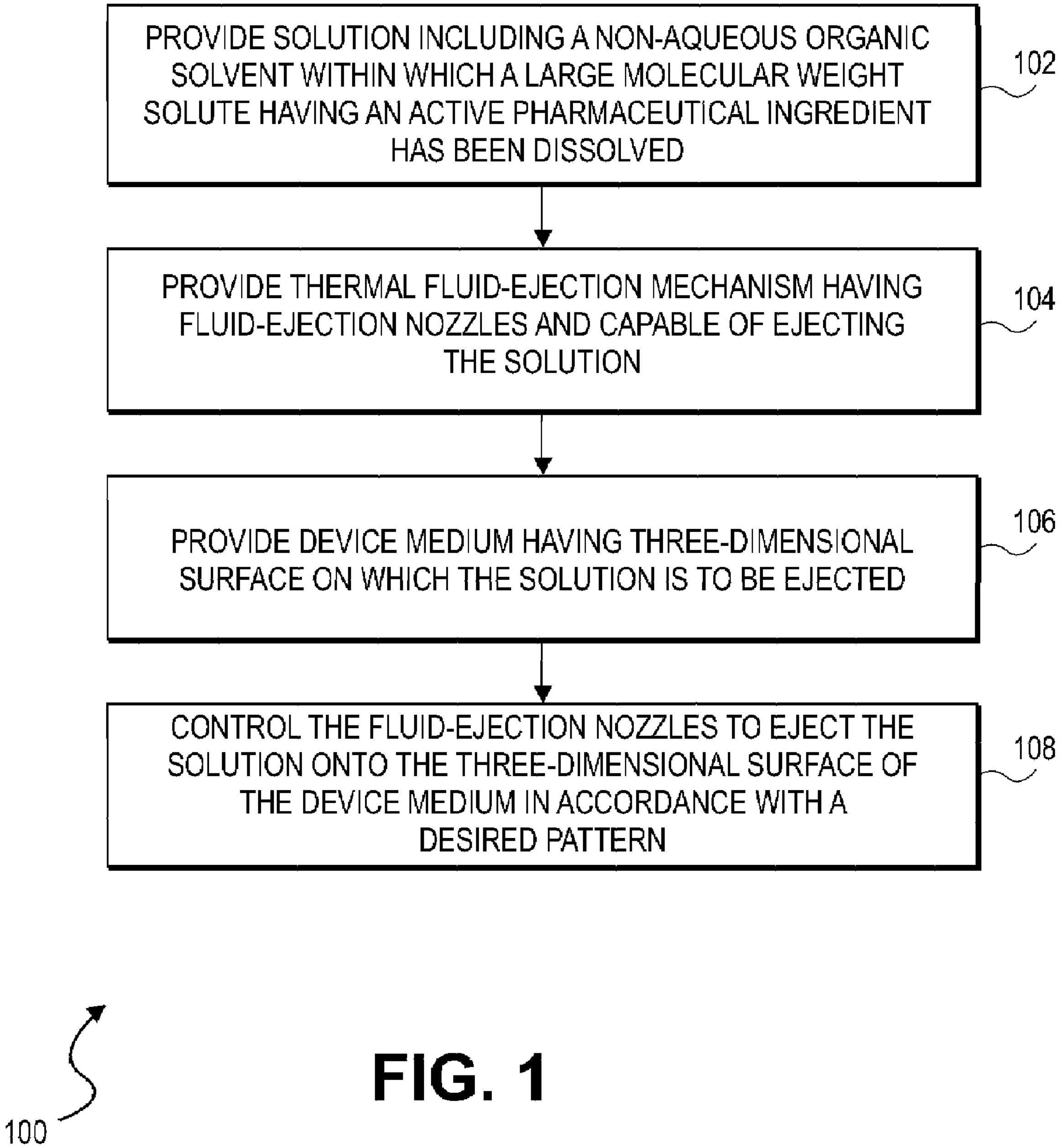
FIG. 1 is a flowchart of a method for ejecting a solution having a large molecular weight solute onto a device medium, according to an embodiment of the invention.

FIG. 1 shows a method 100 for ejecting a solution having a large molecular weight solute onto a device medium to coat the device medium with the solute, according to an embodiment of the invention. A solution is provided that includes a non-aqueous organic solvent within which a large molecular weight solute having an active pharmaceutical ingredient has been dissolved (102). The solvent is non-aqueous in that it is not water and does not contain water. The solvent is organic in that it is not inorganic. Examples of non-aqueous organic solvents include acetone, methanol, ethanol, isopropanol, butanol, butyl alcohol, cyclohexanol, methyl acetate, ethyl acetate, propyl acetate, butyl acetate, and chloromethane.

Additional examples include dichloromethane, trichloromethane, tetrachloroethane, acetone, tetrahydrofuran, methylethylketone, acetonitrile, dimethylsulfoxide and N-methylpyrollidone, and various combinations of these solvents. Further examples include glycerol, 1,2 propane diol, hexane, isobutanol, toluene, and xylene. Desirable solvent compositions are those with a boiling point less than 150 degrees Celsius (° C.). By comparison, ink that is commonly thermally ejected using thermal-inkjet printers is aqueous, in that it contains water.

The term active pharmaceutical ingredient is used in a general and broadly encompassing sense herein. For instance, such an active pharmaceutical ingredient may be a drug. Another type of active pharmaceutical ingredient is a bioactive substance, such as a protein, a biologic, or another type of active pharmaceutical ingredient.

The solute has a large molecular weight in that it has a molecular weight of at least 50,000 atomic mass units (AMU's). The large molecular weight solute may be or include a large molecular weight material like a large molecular weight polymer, a monomer, or a monomer and a polymer. For instance, the solute may include an active pharmaceutical ingredient within a monomer and/or a polymer. The monomer may be capable of being converted to a fully formed polymer. Examples of large molecular weight polymers include homo- and co-polymers of polylactic acid, polyethylene glycol, polyglycolic acid/polylactic acid, polycaprolactone, polyhydroxybutarate valerate, polyorthoester, polyethylenoxide/polybutylene terepthalate, and polyurethane. Additional examples include silicone, polyethylene terephthalate, phosphorylcholine-based polymers and acrylic homo and copolymers of hydroxyethylmethylacrylate, methylacrylate, ethyl acrylate, methyl methacrylate and ethyl methacrylate. Further examples include polycaprolactam, polystyrene-butadiene, chitosan, and alginate-based polymers.

The active pharmaceutical ingredient is disposed within the solute, and may be a drug, or another type of active pharmaceutical ingredient. The presence of the active pharmaceutical ingredient within the solute is typically that which provides the desired benefits of the coating on the device medium when the device medium is implanted or inserted into the human body. By comparison, the purpose of the large molecular weight polymer or other large molecular weight material is primarily to control the time-release profile of the active pharmaceutical ingredient, and ensure that the coating properly adheres to the device medium.

A thermal-fluid ejection mechanism is provided that has multiple fluid-ejection nozzles and that is capable of ejecting the solution (104). An advantage of thermal-fluid ejection mechanisms, as compared to piezoelectric fluid-ejection mechanisms, is that the former can typically have more densely packed fluid-ejection nozzles than the latter can. This is partly why, for instance, prior art piezoelectric fluid-ejection mechanisms for coating device media typically employ just single-nozzle piezoelectric fluid-ejection mechanisms. It can be stated that in general, a thermal-fluid ejection mechanism of an embodiment of the invention can have a greater number and/or more densely packed fluid-ejection nozzles than piezoelectric fluid-ejection mechanisms have for a given device medium-coating application.

Typical thermal-fluid and piezoelectric ejection mechanisms used to eject ink onto paper or other media, as in inkjet-printing devices, are not amenable to thermal ejection of large molecular weight solutes dissolved within non-aqueous organic solvents, as in embodiments of the invention. Rather, such existing thermal-fluid ejection mechanisms have thermal fluid-ejection nozzles that have orifices too small in diameter to properly eject large molecular weight materials without difficulty. Therefore, in one embodiment, the thermal fluid-ejection nozzles of the thermal-fluid ejection mechanism have diameters of at least thirty microns, as compared to, for instance, diameters of at least ten-to-fifteen microns as in modern conventional thermal fluid-ejection nozzles used in inkjet-printing devices.

Furthermore, because the solutions ejected by thermal-fluid ejection mechanisms of embodiments of the invention are non-aqueous and organic, existing thermal-fluid ejection mechanisms used to eject ink, as in inkjet-printing devices, are not inherently suited for thermally ejecting such solutions. That is, while the basic technology for thermal ejection may be the same in both embodiments of the invention and in conventional inkjet-printing applications, the thermal-fluid ejection mechanisms of embodiments of the invention can be considerably and novelly different. Besides the orifices of the thermal fluid-ejection nozzles being larger to manage premature drying within the nozzle, other components of thermal-fluid ejection mechanisms of embodiments of the invention may also differ, as compared to conventional inkjet-printing thermal-fluid ejection mechanisms, to ensure that they can accommodate non-aqueous and organic solvent-based solutions.

For example, because less energy is needed for low-boiling point solvents, which can be employed in embodiments of the invention, the width of the firing pulse may be reduced and the size of resistors within thermal fluid-ejection mechanisms may be increased in embodiments of the invention for such solvents. The materials employed within the fluid-ejection mechanisms may be specific to organic solvents. Other components may also be adjusted or differ as compared to conventional thermal-fluid ejection mechanisms to accommodate non-aqueous and organic solvent-based solutions.

A device medium is provided that has a three-dimensional surface on which the solution in question is to be ejected (106). A device medium is a medium in that it receives the solution as ejected by the thermal fluid-ejection nozzles of the thermal fluid-ejection mechanism. A device medium is further a device in that it has functionality beyond that which is commonly ascribed to media and that the device can perform in relation to the coating ejected thereon, without assistance from other devices.

For example, one type of a device medium is a medical device medium, like a stent, heart implant, or a needle. A stent in particular is inserted into an artery to ensure that the artery stays open, and thus is a device performing this functionality. A drug coating assists in this functionality, by for instance, helping to ensure that the stenosis does not reform, among other things. By comparison, what is commonly referred to as media includes paper, optical media like compact discs, and so on. These types of media are not devices, in that they are incapable of performing any functionality by themselves without the assistance of devices. For example, paper may have human-readable information printed on it, but the paper cannot perform any function related to this information by itself. As another example, an optical disc may have machine-readable data situated on it, but the optical disc cannot perform any function related to this information by itself, and has to be inserted into an optical disc drive in order for the data to be read.

The device medium further has a three-dimensional surface. Such a surface compares to more conventional media that have two-dimensional surfaces. For example, paper, optical media like compact discs, and so on, have flat, planar two-dimensional surfaces. Fluid, such as ink, is ejected onto these types of conventional media based on the presumption that the surfaces thereof on which the fluid is to be ejected are flat. Stated another way, such fluid ejection takes into account the x and y directions of the surfaces of these conventional media, and presumes that the surfaces have no features of interest in the z direction extending upwards or downwards from them. That is, the distance from the point of fluid ejection to the surface is at least substantially constant at all times with such conventional media.

By comparison, the device media in relation to which embodiments of the invention are performed have three-dimensional surfaces on which solutions are to be thermally ejected. These three-dimensional surfaces are non-planar surfaces, such as cylindrical or round surfaces, or more complex types of surfaces. A stent, for example, is cylindrically shaped in general. Furthermore, a stent can be made with a wire mesh, where the individual loops of the mesh are themselves cylindrically shaped. Such a complex surface is three-dimensional because solution ejection has to take into account the z direction extending upwards or downwards from the surface, in addition to the x and y directions of the surface. That is, the distance from the point of solution ejection to the surface varies with such device media.

The fluid-ejection nozzles of the thermal fluid-ejection mechanism are controlled to eject the solution onto the three-dimensional surface of the device medium in accordance with a desired pattern (108). The desired pattern can be the pattern of the resultant coating on the device medium. Generally, the non-aqueous organic solvent evaporates rapidly after being thermally ejected onto the three-dimensional surface of the device medium. Thereafter, just the solute, including the large molecular weight polymer and the active pharmaceutical ingredient, remain as the coating.

The desired pattern can be simple, such as a complete coating of the three-dimensional surface of the device medium, or more complex. For example, the coating may have multiple layers of the same or different polymers and/or active pharmaceutical ingredients, at the same or different concentrations. Some portions of the surface of the device medium may remain uncoated. The coating may have a particular shape or topography. The coating may be smooth or rough. Different manners by which the fluid-ejection nozzles of the thermal fluid-ejection mechanism are controlled to eject the solution onto the three-dimensional surface of the device medium are described in the following sections of the detailed description.

Figure 2A:
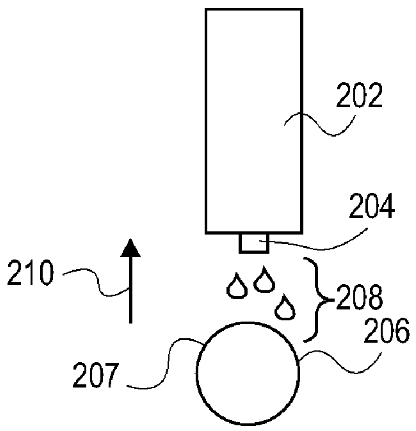
FIG. 2A is a side view diagram of a thermal fluid-ejection mechanism ejecting a solution onto a device medium, according to an embodiment of the invention.

FIG. 2A shows a side view of ejection of a solution 208 by a thermal fluid-ejection mechanism 202 onto a device medium 206, according to a general embodiment of the invention. The thermal fluid-ejection mechanism 202 includes a number of thermal fluid-ejection nozzles 204. The thermal fluid-ejection mechanism 202 works by heating the solution 208 contained within the mechanism 202, causing a small fraction of the solution 208 to nucleate and eject droplets from the thermal fluid-ejection nozzles 204 onto the device medium 206. By comparison, piezoelectric fluid ejection works by moving a flexible membrane, forcing out fluid droplets out the nozzle.

The device medium 206 of FIG. 2A has a three-dimensional surface 207 that is particularly cylindrically shaped. The distance from the fluid-ejection nozzles 204 to the surface 207 of the device medium 206 thus is variable and not constant. The device medium 206 may be a stent, another type of medical device medium, or another type of device medium completely. The solution 208 includes a non-aqueous solvent in which a large molecular weight polymer has been dissolved. The solute includes this large molecular weight polymer and an active pharmaceutical ingredient at a specified concentration.

Figure 2B:
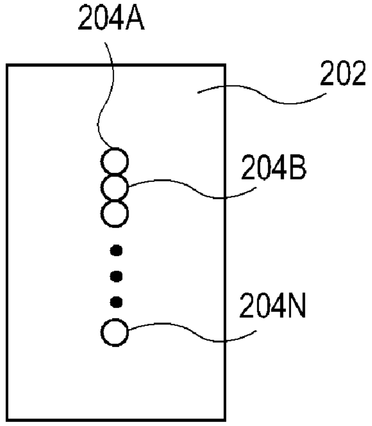
FIG. 2B is a bottom view diagram of a thermal fluid-ejection mechanism, according to an embodiment of the invention.

FIG. 2B shows a bottom view of the thermal fluid-ejection mechanism 202, in the direction of arrow 210 of FIG. 2A, according to an embodiment of the invention. The fluid-ejection mechanism 202 includes thermal fluid-ejection nozzles 204A, 204B, . . . , 204N, which are collectively referred to as the thermal fluid-ejection nozzles 204. The thermal fluid-ejection nozzles 204 each have an orifice size of at least thirty microns in diameter, to permit high concentrations of the large molecular weight solute within the solution 208 to be reliably ejected therethrough.

Figure 2C:
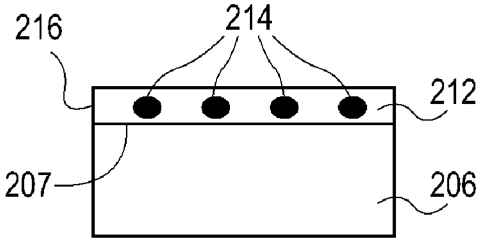
FIG. 2C is a cross-sectional side view diagram of a device medium onto which a coating has resulted from thermal ejection of a solution thereon and after evaporation of a solvent of the solution, according to an embodiment of the invention.

FIG. 2C shows a side view of a cross section of the device medium 207 after the solution 208 has been ejected thereon and after sufficient time has passed such that the solvent of the solution 208 has evaporated, according to an embodiment of the invention. The device medium 207 is depicted as having a flat, two-dimensional surface 207 for illustrative clarity and convenience, but in actuality the surface 207 is a three-dimensional surface, as has been described. Ejection of the solution 208 onto the surface 207, and subsequent evaporation of the solvent therefrom, has resulted in a coating 216 on the three-dimensional surface 207 of the device medium 207. The coating 216 includes a large molecular weight solute 212 having an active pharmaceutical ingredient 214 disposed therein.

It is noted that embodiments of the invention are described in relation to the situation where there is a solute having a polymer containing an active pharmaceutical ingredient. However, other embodiments of the invention are not so limited. For example, the coating 216 may include a number of layers, one or more of which may be formed from solutes that are pure polymer without any active pharmaceutical ingredients. As another example, the coating 216 may itself just include one or more layers of solute, all of which are pure polymer without any active pharmaceutical ingredients.

General Approaches for Moving the Thermal Fluid-Ejection Mechanism

The thermal fluid-ejection mechanism 202 can be moved relative to the three-dimensional surface 207 of the device medium 206 in one of two ways. First, the fluid-ejection mechanism 202 can be moved in accordance with a vector mode of operation. In the vector mode, the mechanism 202 is freely moved in any direction within an x-y plane over the three-dimensional surface 207 until the desired pattern has been formed on the surface 207. Second, the fluid-ejection mechanism 202 can be moved in accordance with a scanning mode of operation. In the scanning mode, the mechanism 202 is moved, or scanned, along an x direction over the three-dimensional surface 207. The mechanism 202 or the three-dimensional surface 207 is then moved in a perpendicular, y direction, and the mechanism 202 is again moved, or scanned, along the x direction over the surface 207. This process is repeated until the desired pattern has been formed on the three-dimensional surface 207.

Figure 3A:
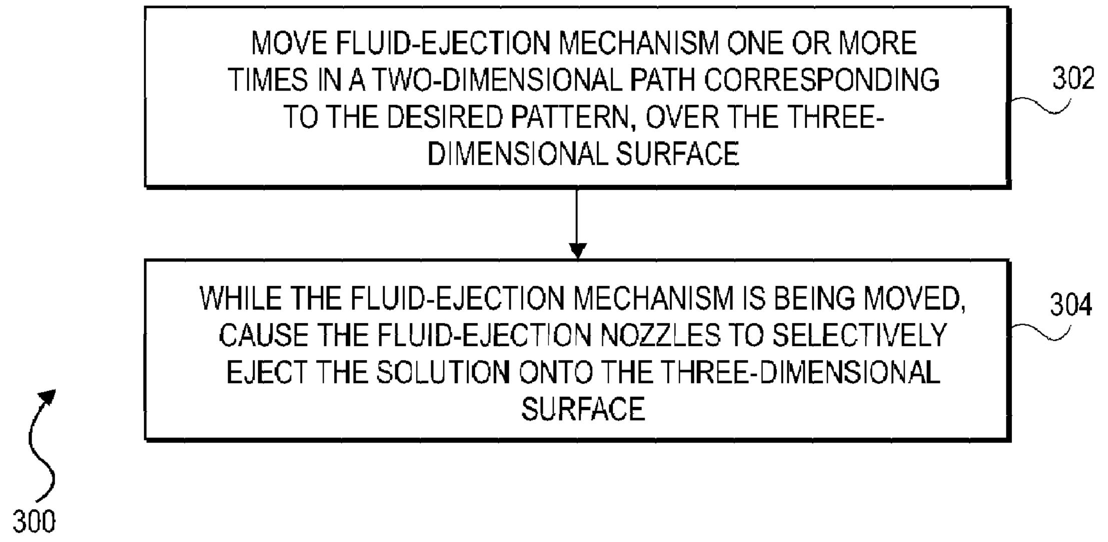
FIG. 3A is a flowchart of a method for moving a thermal fluid-ejection mechanism in a vector mode of operation, according to an embodiment of the invention.

FIG. 3A shows a method 300 for moving the thermal fluid-ejection mechanism 202 relative to the three-dimensional surface 207 of the device medium 206 in accordance with the vector mode, according to an embodiment of the invention. The method 300 may be performed as part of part 108 of the method 100 of FIG. 1. The fluid-ejection mechanism 202 is moved one or more times along a two-dimensional path that corresponds to the desired pattern, over the three-dimensional surface 207 (302). In another embodiment, the path may be three-dimensional, such that the fluid-ejection mechanism 202 is moved along a z-axis up and down, in addition to being moved along the x- and y-axes. While the fluid-ejection mechanism 202 is being so moved, the fluid-ejection nozzles 204 are caused to selectively eject the solution 208 onto the three-dimensional surface 207 in accordance with the desired pattern (304). The fluid-ejection mechanism can be moved more than one time along the path so that multiple layers of the solution 208 is deposited in the same places on the three-dimensional surface 207.

Figure 3B:
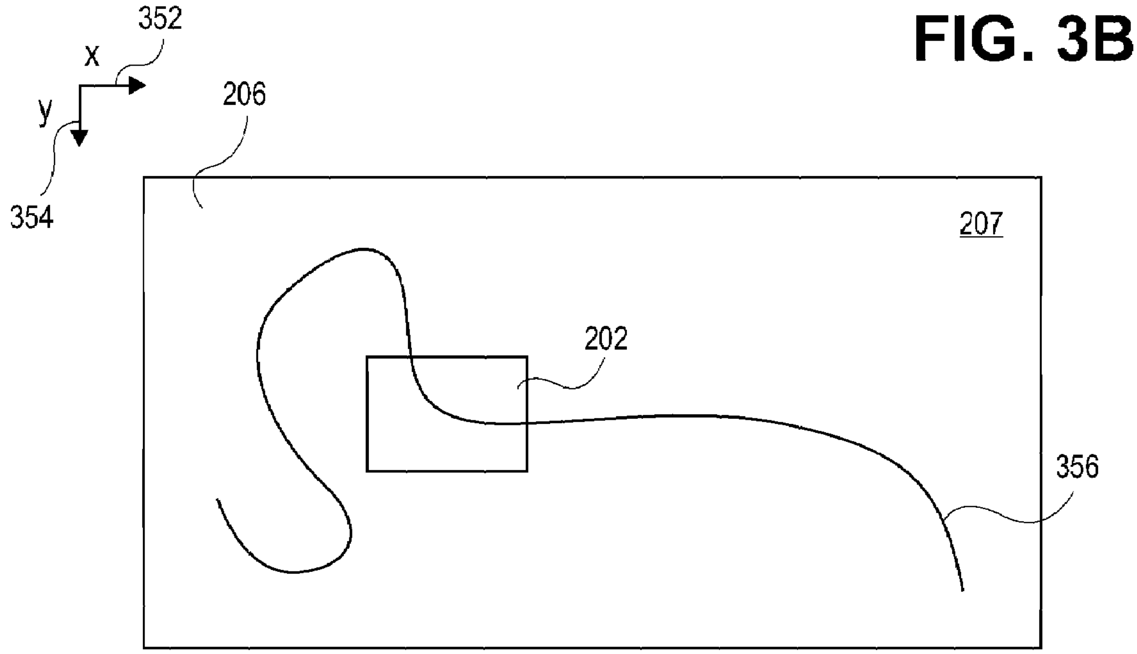
FIG. 3B is a top view diagram showing representative performance of the vector mode of operation of the thermal fluid-ejection mechanism, according to an embodiment of the invention.

FIG. 3B shows a top view of representative performance of the method 300, according to an embodiment of the invention. The three-dimensional surface 207 of the device medium 206 is depicted in FIG. 2B as flat and planar again, for illustrative convenience and clarity. An x-y plane is defined by the x-axis 352 and the y-axis 354. The fluid-ejection mechanism 202 is moved along a path corresponding to the desired pattern 356 to be formed on the three-dimensional surface 207, and the fluid-ejection nozzles 204 of the mechanism 202 selectively eject the solution 208 as needed as the mechanism 202 is moved to realize the pattern 356. Thus, the fluid-ejection mechanism 202 is freely movable in any direction within the plane defined by the x- and y-axes.

Figure 4A:
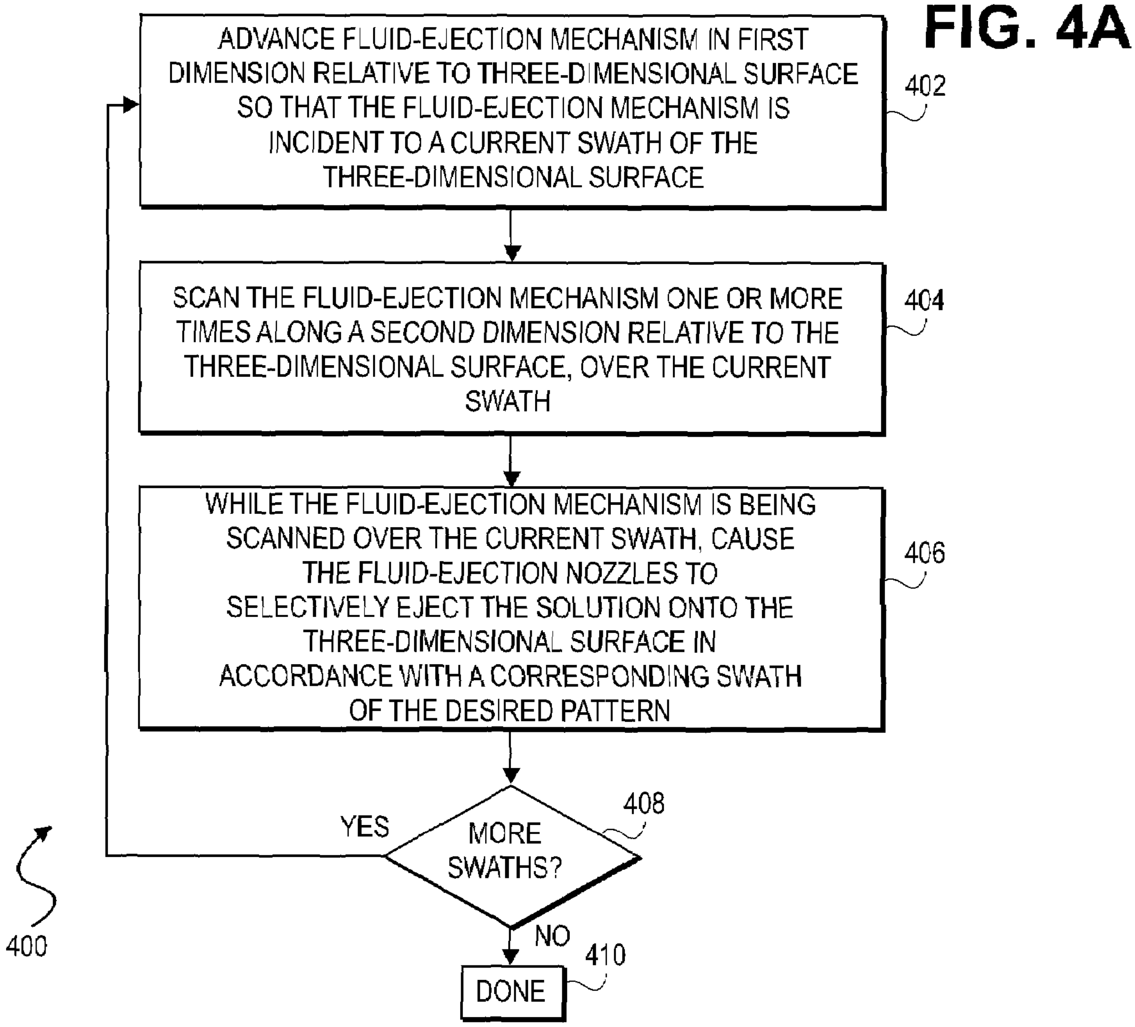
FIG. 4A is a flowchart of a method for moving a thermal fluid-ejection mechanism in a scanning mode of operation, according to an embodiment of the invention.

FIG. 4A shows a method 400 for moving the thermal fluid-ejection mechanism 202 relative to the three-dimensional surface 207 of the device medium 206 in accordance with the scanning mode, according to an embodiment of the invention. The method 400 may be performed as part of part 108 of the method 100 of FIG. 1. The fluid-ejection mechanism 202 is advanced in a first dimension relative to the three-dimensional surface 207 of the device medium 206, so that the fluid-ejection mechanism 202 is incident to a current swath of the surface 207 (402). For example, the device medium 206 may remain stationary, and the fluid-ejection mechanism 202 moved. As another example, the fluid-ejection mechanism 202 may remain stationary, and the device medium 206 moved, such as by being rotated.

The fluid-ejection mechanism 202 is then scanned one or more times along a second dimension relative to the three-dimensional surface 207, over the current swath thereof (404). The second dimension is perpendicular to the first dimension. For example, the first dimension may correspond to the y-axis of a plane, and the second dimension may correspond to the x-axis of the plane. While the fluid-ejection mechanism is being scanned over the current swath, the fluid-ejection nozzles 204 are caused to selectively eject the solution 208 onto the three-dimensional surface 207 in accordance with a corresponding swath of the desired pattern (406). If there are more swaths of the three-dimensional surface 207 that need to have the solution 208 ejected thereon to realize the desired pattern (408), then the method 400 repeats at part 402. Otherwise, the method 400 is finished (410), such that the desired pattern has been formed on the three-dimensional surface 207.

Figure 4B:
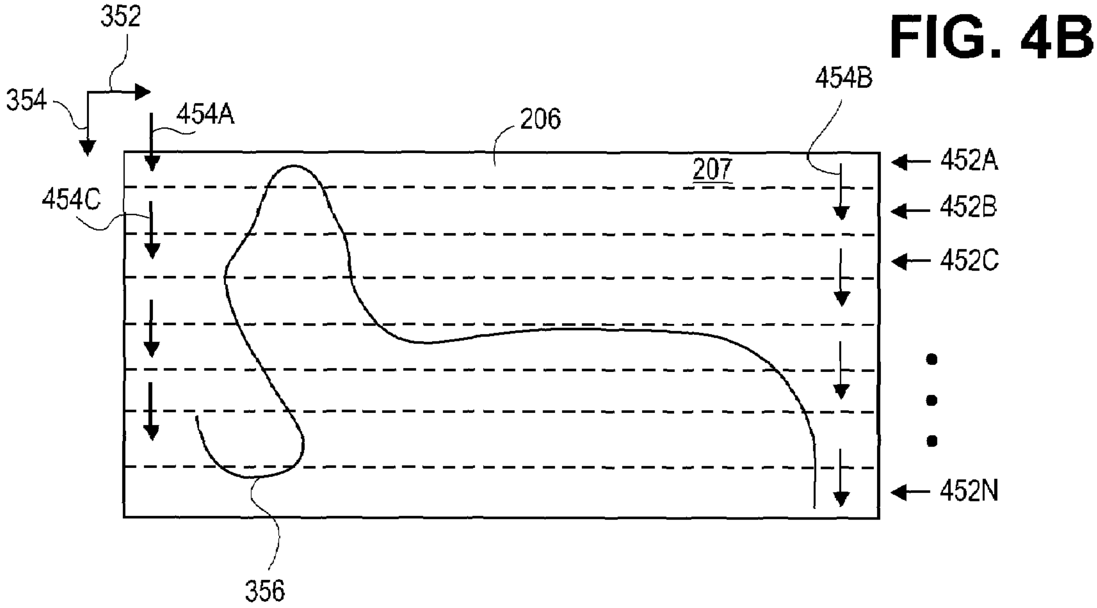
FIG. 4B is a top view diagram showing representative performance of the scanning mode of operation of the thermal fluid-ejection mechanism, according to an embodiment of the invention.

FIG. 4B shows a top view of representative performance of the method 400, according to an embodiment of the invention. The three-dimensional surface 207 of the device medium 206 is depicted in FIG. 2B as flat and planar again, for illustrative convenience and clarity. The x-axis is indicated by the arrow 352, and the y-axis is indicated by the arrow 354, such that an x-y plane is defined by these two axes. The first dimension referred to above corresponds to the dimension defined by the y-axis, and the second dimension referred to above corresponds to the dimension defined by the x-axis.

The three-dimensional surface 207 of the device medium 206 can be considered as being logically divided into a number of swaths 452A, 452B, 452C, . . . , 452N, collectively referred to as the swaths 452. Each swath extends from one side of the surface 207 to another side of the surface 207 along the x-axis. Each swath has a height corresponding to a distance over the surface 207 along the y-axis over which the fluid-ejection mechanism 202 is capable of ejecting the solution 208 at any given time.

Representative performance of the method 400 is particularly described in relation to swaths 452A, 452B, and 452C of FIG. 4B. The fluid-ejection mechanism 202 is advanced along the y-axis relative to the three-dimensional surface 207, as indicated by the arrow 454A, until it is incident to the swath 452A, as the current swath. The fluid-ejection mechanism 202 is then scanned over the swath 452A along the x-axis, and the fluid-ejection nozzles 204 caused to eject the solution 208 as needed to realize the portion of the desired pattern 356 lying within the swath 452A. For example, just a small portion of the swath 452A receives the solution 208, since just a small portion of the pattern 356 lies within the swath 452A. The fluid-ejection mechanism 202 may be scanned over the swath 452 along the x-axis one or more times.

Thereafter, the fluid-ejection mechanism 202 is advanced along the y-axis relative to the three-dimensional surface 207, as indicated by the arrow 454B, until it is incident to the swath 452B, as the new currently swath. The fluid-ejection mechanism 202 is scanned over the swath 452B along the x-axis, and the fluid-ejection nozzles 204 caused to eject the solution 208 as needed to realize the portion of the desired pattern 356 lying within the swath 452B. Next, the fluid-ejection mechanism 202 is advanced along the y-axis relative to the three-dimensional surface 207, as indicated by the arrow 454C, until it is incident to the swath 452C, as the new currently swath. The fluid-ejection mechanism 202 is scanned over the swath 452BC along the x-axis, and the fluid-ejection nozzles 204 caused to eject the solution 208 as needed to realize the portion of desired pattern 356 lying within the swath 452C. This process is repeated for all of the remaining swaths 452, until the desired pattern 356 has been formed on the three-dimensional surface 207 of the device medium 206.

Alternatively, each of the swaths 452 may be traversed a large number of times along the x-axis prior to advancement along the y-axis. For example, there may just be four swaths for a given surface 207. However, the fluid-ejection mechanism 202 may pass back and forth over each of these swaths as many as one hundred times, for instance, ejecting fluid each time. In one embodiment, each pass may be considered a swath. Thus, in one embodiment, successive swaths may be considered coincidental, or "on top of" one another, such that there is no motion along the y-axis in-between some of the swaths, which is not particularly depicted in FIG. 4B. In such an example, multiple layers of solute, via multiple passes of the fluid-ejection mechanism over the same locations of the surface 207, are achieved. For instance, there may be one-hundred or more such passes over the same locations of the three-dimensional surface 207.

In such an embodiment, as well as other embodiments, each of the swaths 452 may be considered as corresponding to one of the fluid-ejection nozzles 204 of the fluid-ejection mechanism 202. Thus, the fluid-ejection mechanism 202 moves back and forth over the surface 207. Each of the nozzles 204 is responsible for ejecting the solution 208 onto a different y-position of the surface 207.

Decapping, and Preventing Plugging of the Fluid-Ejection Nozzles

Figure 5A:
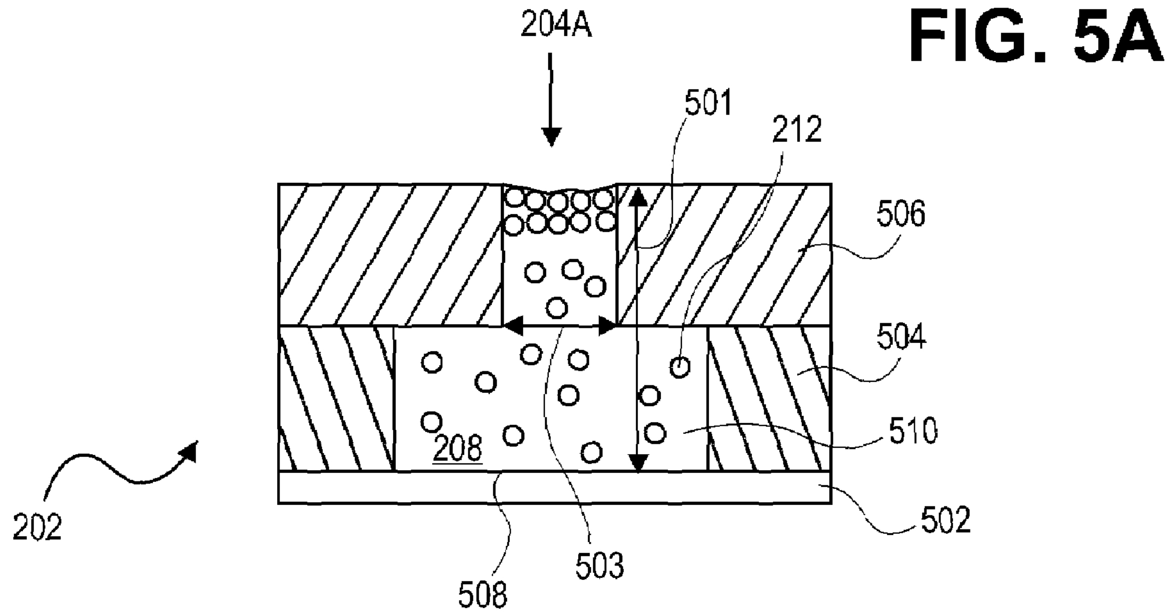
FIG. 5A is a diagram depicting undesirable viscous plug formation at the meniscus of a fluid-ejection nozzle of a thermal fluid-ejection mechanism, according to an embodiment of the invention.

FIG. 5A shows undesirable plugging, clogging, or "skinning over" of the meniscus of the fluid-ejection nozzle 204A of the thermal fluid-ejection mechanism 202 that can result, according to an embodiment of the invention. Nozzle clogging occurs when the solution 208 plugs up a fluid-ejection nozzle, such that the fluid-ejection mechanism 202 is unable to eject the solution 208 through the nozzle. The fluid-ejection mechanism 202 is depicted as including a substrate 502, a barrier layer 504, and an orifice layer 506. A cavity 508 is defined within the barrier layer 504, from which the nozzle 204A extends through the orifice layer 506.

The solution 208 is situated within the cavity 508 and the fluid-ejection nozzle 204A. The solution 208 includes solvent 510, within which the large molecular weight solute 212 is disposed, the latter indicated by circles in FIG. 5A. Where the fluid-ejection nozzle 204A sits in an open position for a sufficiently long period of time, the solvent 510 at the opening of the fluid-ejection nozzle 204A—that is, at the meniscus of the solution 208—evaporates, leaving an inordinate amount of the solute 212 within this area, a process which is referred to as decapping. Because the solute 212 is a solid, it forms a skin over the opening of the fluid-ejection nozzle 204A, effectively plugging up the nozzle 204A. Plugging of the nozzle 204A prevents it from ejecting droplets of the solution 208. In one embodiment, as is described in more detail below, spitting of the nozzle 204A is achieved to clear the nozzle 204A when plugging occurs.

Figure 5C:
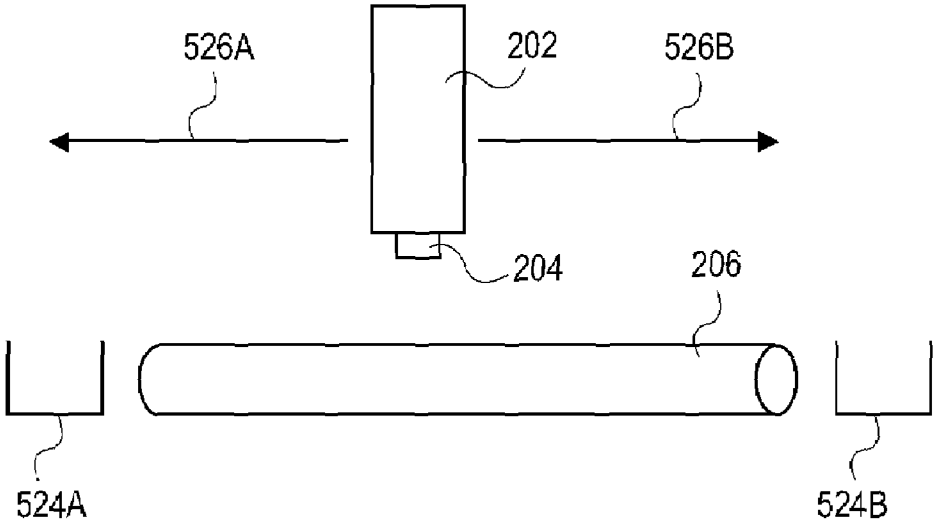
FIG. 5C is a diagram depicting a spitting process that can be performed by fluid-ejection nozzles of a thermal fluid-ejection mechanism, according to an embodiment of the invention.
Figure 5B:
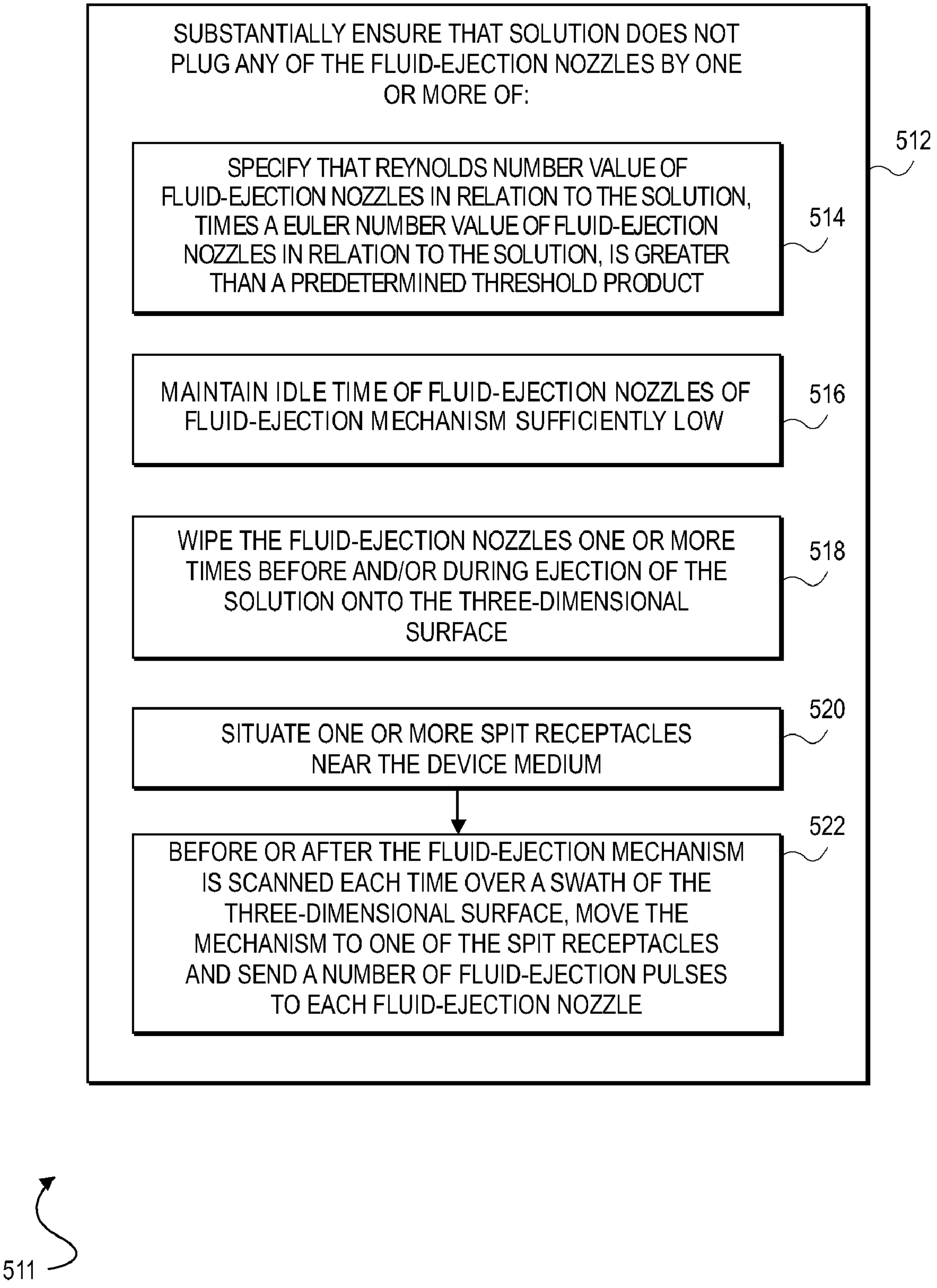
FIG. 5B is a flowchart of a method for substantially ensuring that fluid-ejection nozzles of a thermal fluid-ejection mechanism do not become clogged, or plugged, according to an embodiment of the invention.

FIG. 5B shows a method 511 for substantially ensuring that the solution 208 does not plug any of the fluid-ejection nozzles 204 of the thermal-ejection mechanism 202, according to an embodiment of the invention. The method 511 may be performed as part of part 108 of the method 100 of FIG. 1. The method 511 substantially ensures that the solution 208 does not plug any of the fluid-ejection nozzles (512), by performing one or more of part 514, part 516, part 518, and parts 520 and 522. Each of these parts is now described in detail.

First, the Reynolds Number value of the fluid-ejection nozzles 204 relative to the solution 208, times a Euler Number value of the fluid-ejection nozzles 204 relative to the solution 208, can be specified such that it is greater than a predetermined threshold product (514). It has been determined that, where the Reynolds Number value times the Euler Number value are greater than a predetermined threshold product of ten, for instance, plugging up of the fluid-ejection nozzles 204 with the solution 208 is substantially less likely to occur. The Reynolds Number value is the ratio of the inertial force to the viscous force within a fluid flow. The Euler Number value is the ratio of the pressure force generated by phase change (in this case, the transient boiling or nucleation of the liquid) to the inertial force in a flow.

In one embodiment using a circular nozzle, the product of the Reynolds Number value and the Euler Number value can be approximated as:

$$Re \times Eu = \frac{\pi R^4 \Delta\rho}{8\mu QL} \quad (1)$$

In equation (1), Re is the Reynolds Number value and Eu is the Euler Number value. R is the radius of the fluid-ejection nozzle, which is half the distance of the diameter indicated by the line 503 in FIG. 5A. Δp is the gauge pressure that is created by sudden nucleation (boiling) of the solution within the nozzle, which operates for a few microseconds at most. μ is the effective viscosity of the solution 208, whereas Q is the volumetric flow rate of the solution 208 through the fluid-ejection nozzle. L is the distance indicated by the line 501 in FIG. 5A.

The product of equation (1) can also be considered the ratio of nucleation force to viscous force. The nucleation force within a thermal fluid-ejection process is the pressure in the vapor bubble created by suddenly heating the solution 208 multiplied by the projected area of the bubble. The viscous force is a function of the flow resistance of the solution 208 through the nozzle. Thus, for ejection to result, the nucleation force has to be much larger than the viscous force, such as by a factor of ten.

Specifying the product of equation (1) so that it is greater than ten can be achieved in a number of different ways. Δp can be increased by increasing the temperature employed during the thermal fluid-ejection process, or by changing the solvent to one that has a higher critical temperature and other appropriate thermophysical properties, for instance. Increasing the diameter of the fluid-ejection nozzle increases its radius R, which has a very strong effect on the product in equation (1). The effective viscosity in the jetting chamber μ can be decreased by adding a humectant to the solution 208 to reduce the rate of evaporation of the solvent 510.

Still referring to FIG. 5B, another approach to substantially ensure that the solution 208 does not plug any of the fluid-ejection nozzles 204 is to maintain the idle time, which is time between successive droplet ejections from a given nozzle, sufficiently low (516). This can be achieved in a variety of different ways. First, the fluid-ejection mechanism 200 may be moved relatively quickly, so long as aerodynamic effects that may hasten decapping and cause droplet misdirection do not occur. Second, the fluid-ejection mechanism 200 and its nozzles 204 may be oriented relative to the part to be coated so that no nozzle is left idle for an inordinately long time. Third, a nozzle may be spit within a spitting receptacle if more than a threshold idle time has been exceeded. Fourth, a nozzle may be wiped if an even longer threshold time has been exceeded.

Therefore, for a given distance between ejection locations (i.e., between ejection pixel locations), a predetermined threshold rate of movement of the fluid-ejection mechanism 202 can be experimentally determined, corresponding to the maximum allowable idle time, corresponding to the time above which plugging of the fluid-ejection nozzles 204 of the thermal fluid-ejection mechanism 202 is likely to occur. Thereafter, moving the fluid-ejection mechanism 202 in the vector mode of operation or in the scanning mode of operation at a rate greater than or equal to this predetermined threshold rate makes plugging of the fluid-ejection nozzles less likely to occur. For instance, in the scanning mode in particular, the fluid-ejection mechanism 202 is scanned over the three-dimensional surface 207 at a rate greater than or equal to the predetermined threshold rate.

Still referring to FIG. 5B, a third approach to substantially ensure that the solution 208 does not plug any of the fluid-ejection nozzles 204 is to wipe the fluid-ejection nozzles 204 one or more times before and/or during ejection of the solution 208 onto the three-dimensional surface 207 (518). Wiping the fluid-ejection nozzles 204 can involve, for instance, moving the fluid-ejection mechanism 202 to a servicing area, at which the nozzles 204 can be wiped against a wiping medium, like cloth (which may be either dry or wet) or another type of wiping medium. Wiping the fluid-ejection nozzles 204 in this way serves to clean the nozzles 204 of any dried solute 212 thereon, such that subsequent plugging of the nozzles 204 is less likely to occur.

For example, consider the scanning mode of operation of FIG. 4B. In one embodiment, after each scan of the fluid-ejection mechanism 202 from left to right and/or from right to left over one of the swaths 452, the fluid-ejection mechanism 202 may be moved to a servicing area at which the fluid-ejection nozzles 204 can be wiped. In another embodiment, before and/or after each time the fluid-ejection mechanism 202 is advanced along the y-axis 354, as exemplarily represented by the arrows 454A, 454B, and 454C, for instance, the fluid-ejection mechanism 202 may be moved to a servicing area at which the fluid-ejection nozzles 204 can be wiped.

Referring back to FIG. 5B, a fourth approach to substantially ensure that the solution 208 does not plug any of the fluid-ejection nozzles 204 is to situate one or more spit receptacles near the device medium 206 (520). In one embodiment, utilization of such spit receptacles may be the primary manner by which prevention of plugging is achieved. Thereafter, before or after the fluid-ejection mechanism 202 is scanned over one of the swaths 452 of the three-dimensional surface 207, the mechanism 202 is moved to the closest spit receptacle and caused to undergo a process known as spitting (522). In coating device media that have non-critical-to-function areas, as known within the art, and less rigid constraints on coating mass variations, such receptacles may also be positioned as part of the pattern itself, on the device media, and/or underneath the device media where the media has holes through which spitting can occur.

Spitting involves sending a number of fluid-ejection pulses to each of the fluid-ejection nozzles 204. The fluid-ejection pulses sufficiently heat the solution 208 to ultimately cause the fluid-ejection nozzles 204 to eject the solution 208, breaking through and thus expelling any of the solute 212 that may have skinned over the nozzles 204, and thus ensuring that drop ejection onto the target will reliably occur, because the idle time between nozzle servicing and actual coating/ejection has been minimized. Desirably each pulse causes the ejection of a droplet of the solution 208 from a fluid-ejection nozzle. However, where the fluid-ejection nozzle has been plugged a number of pulses may be needed to break through the solute 212 that has skinned over the nozzle.

FIG. 5C shows representative performance of the spitting of parts 520 and 522 of the method 511, according to an embodiment of the invention. The fluid-ejection mechanism 202, with the fluid-ejection nozzles 204, is situated over the device medium 206. Near to the sides of the device medium 206 spit receptacles 524A and 524B, collectively referred to as the spit receptacles 524, are positioned. Where the fluid-ejection mechanism 202 is to scan left to right relative to the device medium 206, it may beforehand move to the spit receptacle 524A and spit, or afterwards move to the spit receptacle 524B and spit. Likewise, where the fluid-ejection mechanism 202 is to scan right to left relative to the device medium 206, it may beforehand move to the spit receptacle 524B and spit, or afterwards move to the spit receptacle 524A and spit.

Figure 5D:
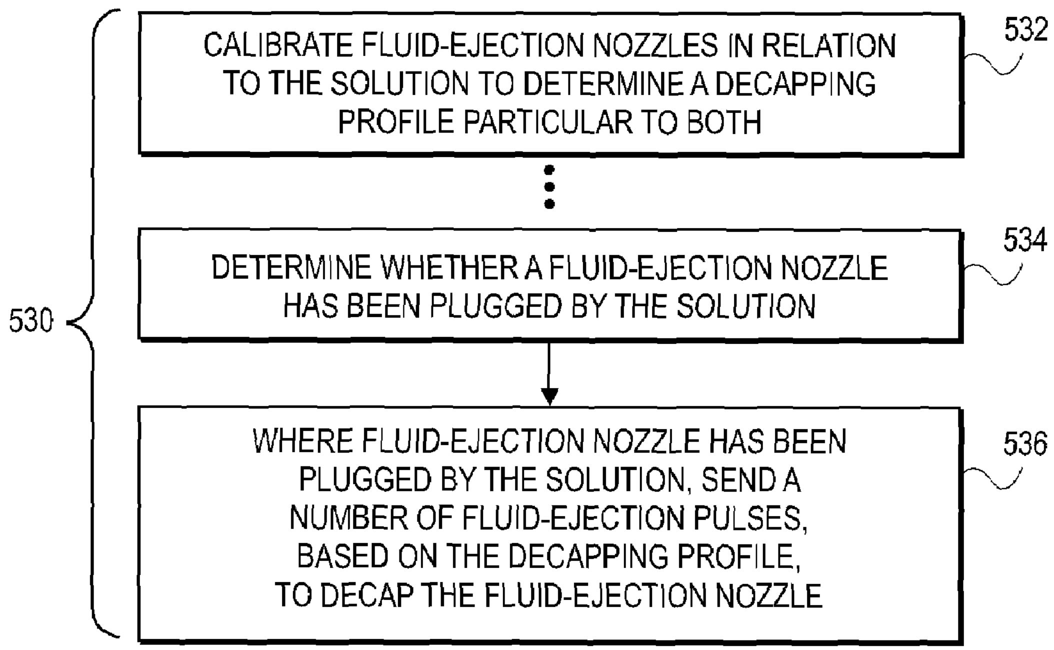
FIG. 5D is a flowchart of a method for preventing clogging of a fluid-ejection nozzle of a thermal fluid-ejection mechanism by using a constructed profile, according to an embodiment of the invention.

FIG. 5D shows a method 530 for servicing a fluid-ejection nozzle of the thermal fluid-ejection mechanism 202 that has been plugged, or clogged, according to an embodiment of the invention. Part 532 of the method 530 may be performed as an additional part of the method 100 of FIG. 1. By comparison, parts 534 and 536 may be performed as part of part 108 of the method 100.

The fluid-ejection nozzles 204 of the thermal fluid-ejection mechanism 202 are calibrated in relation to the solution 208 to determine a profile that is particular to both the specific nozzles 204 that are being used and the specific solution 208 that is being used (532). A profile specifies the number of fluid-ejection pulses that have to be sent to a plugged fluid-ejection nozzle to unplug the fluid-ejection nozzle, as a function of the length of time in which the nozzle has remained unused. For example, the longer a fluid-ejection nozzle has remained unused, the stronger the solute 212 that has skinned over and plugged the nozzle is, and, as a result, the greater number of pulses that have to be successively sent to the fluid-ejection nozzle to clear, or unplug, it.

Calibration of the fluid-ejection nozzles 204 in relation to the solution 208 to determine the particular profile is an experimental process. For example, droplets may be ejected from the fluid-ejection nozzles 204, and then a predetermined amount of time waited. Where the nozzles 204 become plugged after this predetermined amount of time, the number of fluid-ejection pulses that have to be sent to the nozzles 204 to unplug them are counted. This process is repeated a number of times, for different predetermined amounts of time, in order to construct the resulting profile.

Figure 5E:
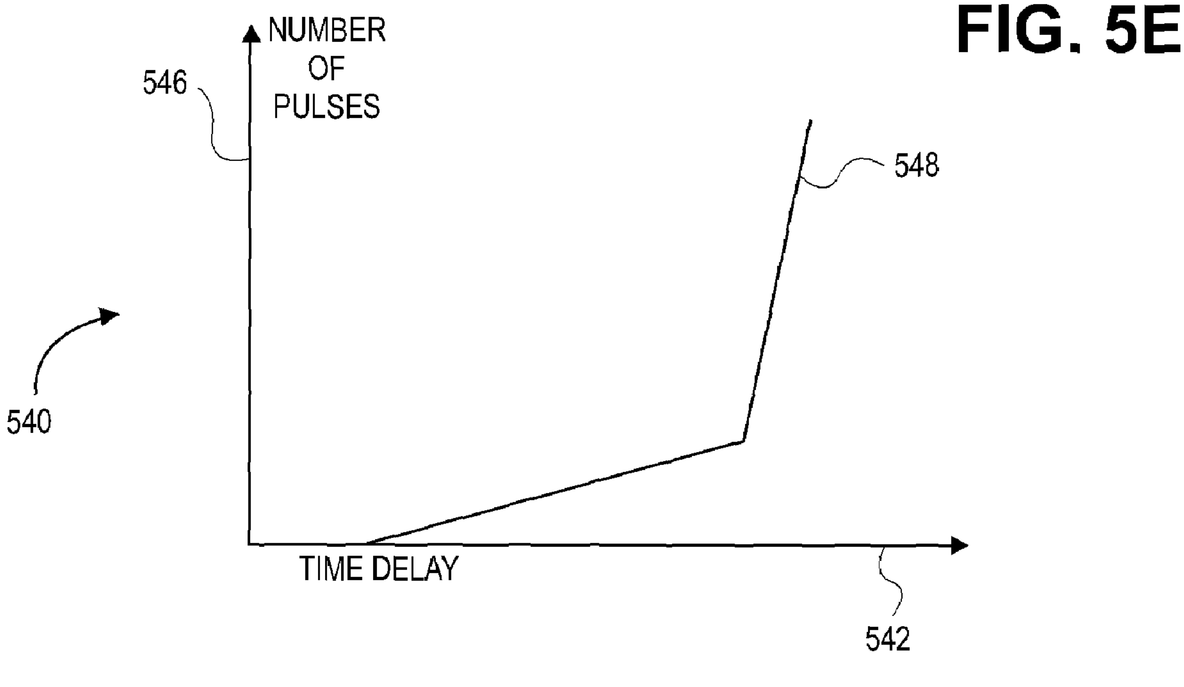
FIG. 5E is a graph of an example profile that can be used to assist in recovering and/or servicing a fluid-ejection nozzle of a thermal fluid-ejection mechanism, according to an embodiment of the invention.

FIG. 5E shows a graph 540 of an example profile, according to an embodiment of the invention. The x-axis 542 denotes time, whereas the y-axis 546 denotes number of pulses. The line 548 corresponds to a profile. The number of pulses needed to clear a plugged fluid-ejection nozzle is looked up as a function of the length of time since the fluid-ejection nozzle last ejected fluid.

Therefore, referring back to FIG. 5D, at some point a determination may be made as to whether a given fluid-ejection nozzle has been plugged by the solution 208 (534). This determination can be presumed after a certain length of time has elapsed since the last time the fluid-ejection nozzle has been used. This determination can be performed in another way as well. For example, the fluid-ejection mechanism 202 may be moved to a drop detector, and the fluid-ejection nozzle in question fired. If the drop detector detects that the fluid-ejection nozzle has ejected a droplet of the solution 208 then the nozzle is not plugged, and otherwise it is.

Where the fluid-ejection nozzle has been plugged by the solution 208, a number of fluid-ejection pulses are sent to the fluid-ejection nozzle to unclog or clear the nozzle (536). For example, the fluid-ejection mechanism 202 may be moved to one of the spit receptacles 524A and 524B. Thereafter, the number of pulses needed to clear the fluid-ejection nozzle is determined using the previously constructed profile, and then sent to the nozzle. Verification of effective nozzle servicing may be performed by using a drop detector, in another way, or no nozzle function verification may be performed.

Accelerating Evaporation of Solvent from Three-Dimensional Surface

The coating 216, including the large molecular weight solute 212 with the active pharmaceutical ingredient 214 therein, is established on the three-dimensional surface 207 of the device medium 206 by first thermally ejecting the solution 208 on the surface 207. Thereafter, the solvent 510 evaporates from the solution 208, leaving primarily the solute 212 and the active pharmaceutical ingredient 214 to form the coating 216. To limit movement of the solution 208 prior to evaporation of the solvent 510, and to otherwise better control the topography of the coating 216 on the three-dimensional surface 207 of the device medium 206, evaporation of the solvent 510 may be actively accelerated.

Figure 6A:
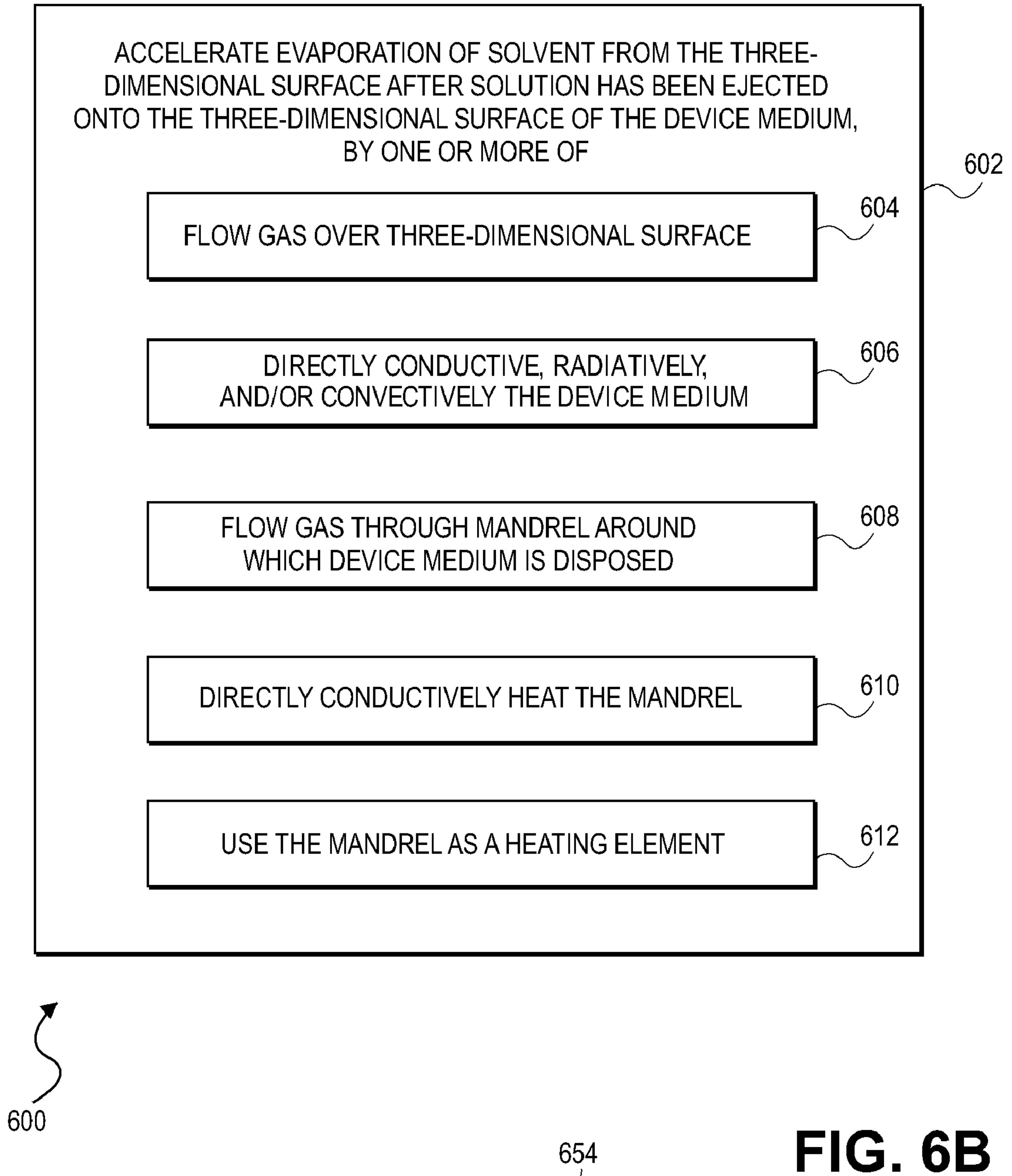
FIG. 6A is a flowchart of a method for accelerating evaporation of a solvent from a solution thermally ejected onto a device medium, according to an embodiment of the invention.

FIG. 6A shows a method 600 for accelerating evaporation of the solvent 510 from the solution 208 as thermally ejected onto the three-dimensional surface 207 of the device medium 206, according to an embodiment of the invention. The method 600 may be performed as part of part 108 of the method 100 of FIG. 1. Such evaporation acceleration (602) can be achieved by performing one or more of parts 604, 606, 608, 610, and 612 of the method 600. Each of these parts is now described in detail.

First, gas may be forced to flow over the three-dimensional surface 207 of the device medium 206 after the solution 208 has been thermally ejected onto the surface 207 (604). The gas may be nitrogen gas, or another type of gas. The gas may be preheated, and may be dry. Flowing such a gas over the three-dimensional surface 207 accomplishes forced convective heat and mass transfer, accelerating evaporation of the solvent 510 from the solution 208 thermally ejected onto the surface 207.

Second, the device medium 206 may itself be directly heated, either by radiation, convection, and/or conduction (606). For example, a heating element may be positioned near the three-dimensional surface of the device medium 206. The heat emanating from the heating element conductively heats the device medium 206. Such conductive and/or radiative heating is direct in that the heat emanating from the heating element directly heats the device medium 206, as opposed to first heating an intermediary component such that the heat from the heating element indirectly conductively heats the device medium 206. Directly conductively heating the device medium 206 accelerates evaporation of the solvent 510 from the solution 208 thermally ejected on the three-dimensional surface 207 of the device medium 206.

Third, gas or liquid may be forced to flow through a mandrel around which the device medium 206 is disposed (608). For example, the device medium may be a stent, or otherwise substantially cylindrically shaped and hollow. In such an embodiment, the stent can be wrapped around a mandrel. Where the mandrel itself is hollow, gas, such as nitrogen gas or another type of gas, and which may be preheated, is flowed through the mandrel. Flowing such a gas through the mandrel heats the device medium and the solvent on it, increasing the solvent's vapor pressure and thus accelerating evaporation of the solvent 510 from the solution 208 thermally ejected onto the surface 207.

Fourth, the mandrel around which the device medium 206 is disposed may be directly conductively heated (610). For example, a heating element may be positioned near the mandrel. The heat emanating from the heating element conductively heats the mandrel. In turn, heating of the mandrel causes heating of the device medium 206. That is, direct conductive heating of the mandrel indirectly conductively heats the device medium 206, which also accelerates evaporation of the solvent 510 from the solution 208 thermally ejected on the three-dimensional surface 207 of the device medium 206.

Fifth, the mandrel itself may be employed as a heating element (612). For instance, the mandrel may be fabricated from or include a resistive heating material, around which an electrical insulator is wrapped, such that the device medium 206 is disposed around the electrical insulator of the mandrel. Where the mandrel includes or is such a resistive heating material, the mandrel itself can function as a heating element. The heat emanating from the mandrel thus conductively heats the device medium 206. Such conductive heating is direct in that the heat emanating from the mandrel directly heats the device medium 206. Employing the mandrel as a heating element that directly conductively heats the device medium 206 accelerates evaporation of the solvent 510 from the solution 208 thermally ejected on the three-dimensional surface 207 of the device medium 206.

Figure 6B:
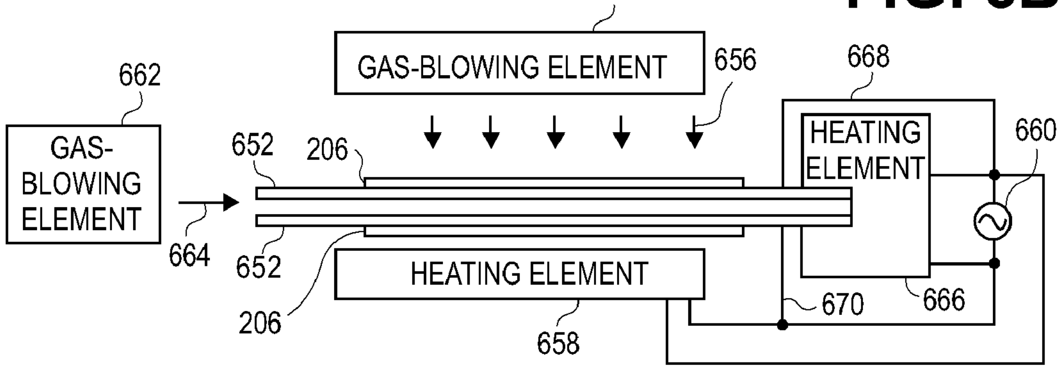
FIG. 6B is a diagram illustratively depicting accelerated evaporation of a solvent from a solution thermally ejected onto a device medium, according to an embodiment of the invention.

FIG. 6B is a cross-sectional diagram illustratively depicting representative performance of parts 604, 606, 608, 610, and 612 of the method 600, according to an embodiment of the invention. Not all parts 604, 606, 608, 610, and 612 have to be performed to achieve accelerated evaporation of the solvent 510 from the solution 208. Rather, just one or more of the parts 604, 606, 608, 610, and 612 can be performed. The device medium 206 is situated on a mandrel 652 in FIG. 6B, and the mandrel 652 is specifically depicted as being hollow.

In part 604, a gas-blowing element 654 is positioned relative to the device medium 206. Warm and dry gas, indicated by arrows 656, is flowed over the device medium 206 to achieve accelerated evaporation. The gas-blowing element 654 may be revolved around the device medium 206, or the device medium 206 itself may be rotated relative to the gas-blowing element 654. It is noted that furthermore the gas flow may be periodically interrupted to ensure that the droplets being ejected onto the surface 207 are not blown off-course by this gas flow. In part 606, a resistive heating element 658 is connected to a power supply 660 to resistively heat the heating element 658. Heat emanating from the heating element 658 directly conductively heats the device medium 206 to achieve accelerated evaporation. That is, heat rises from the heating element 658, convectively heating the device medium 206.

In part 608, a gas-blowing element 662 is at a positive pressure relative to the mandrel 652. Warm and dry gas, indicated by arrow 664, is flowed through the mandrel 652, which is hollow. The heat increases the solvent temperature, increasing its vapor pressure and thus increasing the evaporation rate. In part 610, a resistive heating element 666 is connected to the power supply 660 to resistively heat the heating element 666. Heat emanating from the heating element 666 directly conductively heats the mandrel 652, which indirectly conductively heats the device medium 206 to achieve accelerated evaporation.

Finally, in part 612, the mandrel 652 itself functions as a resistive heating element that is connected to the power supply 660, as indicated by lines 668 and 670. The mandrel 652 may have an electrically insulated material surrounding it (not shown in FIG. 6B) so that electricity does not flow through the device medium 206 itself, which may be electrically conductive. The mandrel 652 may further be thermally insulated as well. Heat emanating from the mandrel 652 directly conductively heats the device medium 206, accelerating evaporation.

It is noted that while just one power supply 660 is depicted in FIG. 6B, there may be different power supplies for each of the different approaches of parts 606, 610, and 612. That is, the heating approaches of parts 606, 610, and 612 are independent of one another. As such, each heating approach may be used by itself, or in conjunction with one or more of the other approaches.

Thickness Control of Coating

Besides having the desired pattern 356, the coating 216, including the large molecular weight solute 212 with the active pharmaceutical ingredient 214 therein, that is established on the three-dimensional surface 207 of the device medium 206 may have a desired thickness. The thickness of the coating 216 after the solution 208 has been thermally ejected onto the three-dimensional surface 207, and after the solvent 510 has evaporated from the solution 208. The thickness of the coating 216 in this respect can be considered the thickness of the solute 212 after thermal ejection of the solution 208 and after evaporation of the solvent 510 from the thermally ejected solution 208.

Figure 7A:
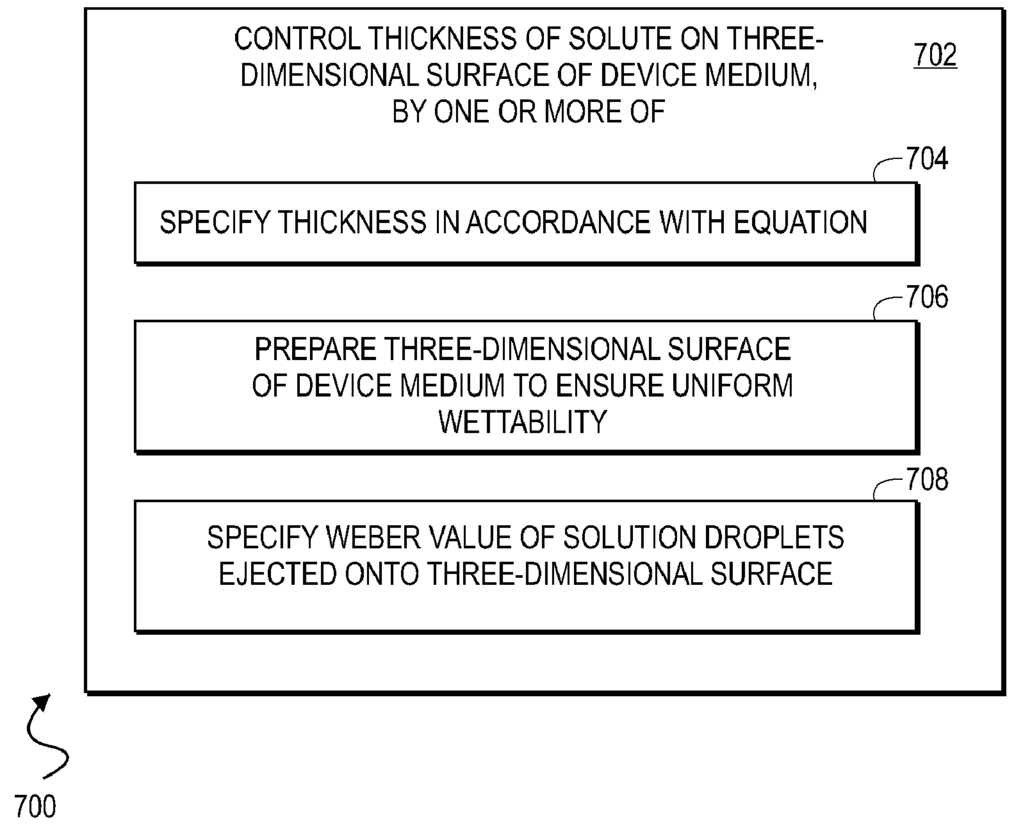
FIG. 7A is a flowchart of a method for controlling the coating on a device medium resulting from thermal ejection of a solution onto the device medium, according to an embodiment of the invention.

FIG. 7A shows a method 700 for controlling the thickness of the coating 216 on the three-dimensional surface 207 of the device medium 206, according to an embodiment of the invention. The method 700 may be performed as part of part 108 of the method 100 of FIG. 1. Controlling the thickness of the coating 216—i.e., the solute 212 (702)—can be achieved by performing one or more of parts 704, 706, and 708. Each of these parts is now described in detail.

First, the thickness of the coating 216 can be controlled by specifying the thickness in accordance with an equation, where the various parameters of the equation are themselves controllable (704). This equation in one embodiment is:

$$t = \frac{N_{pass} c V_{drop} (N_{nozz} - 1)}{\rho \Delta \times [(N_{nozz} - 1)\Delta y + 2M]}. \quad (2)$$

It is noted that equation (2) is for multiple nozzles within an array, where $N_{nozz}$ is greater than one. By comparison, for single nozzle fluid ejection on a surface, the corresponding equation is $$t = \frac{N_{pass} c V_{drop}}{\rho \Delta \times (2M)}. \quad (3)$$

In equations (2) and (3), t is the thickness of the solute 212 (i.e., the coating 216), and $N_{pass}$ is the number of passes of the thermal fluid-ejection mechanism 202 over the three-dimensional surface 207 in which the solution 208 is ejected onto the surface 207. Furthermore, c is the concentration of the solute 212 within the solvent 510, $V_{drop}$ is the volume of a droplet of the solvent 510 ejected by a fluid-ejection nozzle, $N_{nozz}$ (in just the former equation) is the number of the fluid-ejection nozzles 204 actively ejecting the solution 208 onto the three-dimensional surface 207, and ρ is the density of the solute 212 on the three-dimensional surface 207 after evaporation of the solvent 212. Finally, Δx and Δy together are spatial resolutions of the droplets ejected along dimensions x and y, and M is a spreading margin factor, as will be described. Thus, by controlling one or more of these parameters, the thickness of the coating 216 is correspondingly controlled.

Figure 7B:
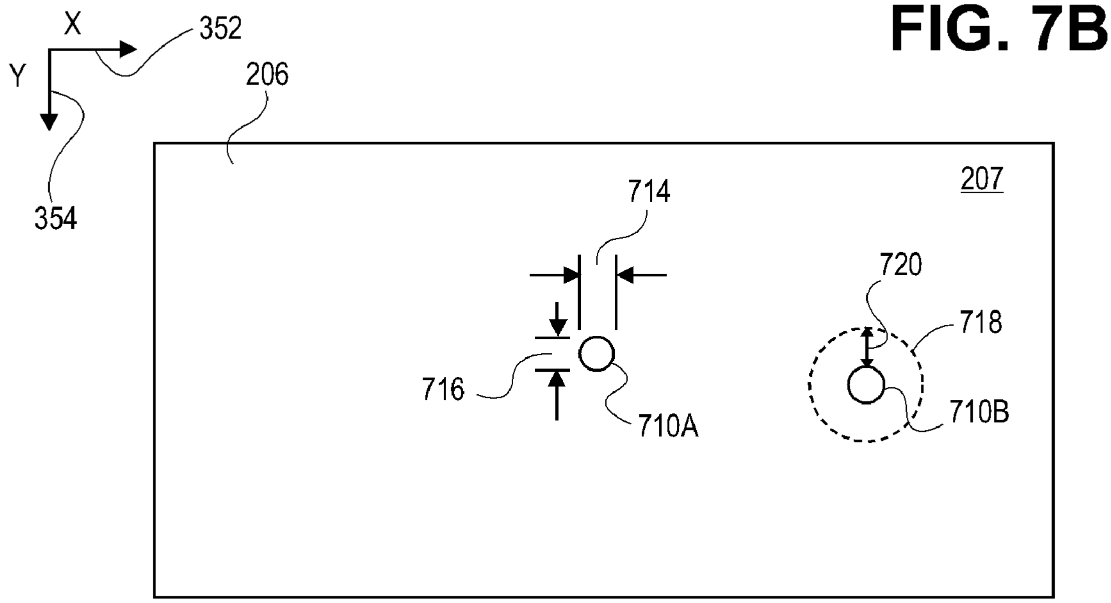
FIG. 7B is a diagram illustratively depicting three of the parameters that can be controlled in the method of FIG. 7A, according to an embodiment of the invention.

FIG. 7B illustratively depicts parameters Δx, Δy, and M of equation (2), according to an embodiment of the invention. A top view of the three-dimensional surface 207 of the device medium 206 is specifically shown in FIG. 7B, where the x-axis 352 and the y-axis 354 are particularly identified. Two representative solution droplets 710A and 710B are also shown in FIG. 7B, which are greatly exaggerated in size for illustrative clarity. Reference number 714 corresponds to parameter Δx, which is the spatial resolution of the solution droplet 710A along the x-axis 352. Similarly, reference number 716 corresponds to parameter Δy, which is the spatial resolution of the solution droplet 710B along the y-axis 354.

Once a droplet of the solution 208 has been thermally ejected onto the three-dimensional surface 207 of the device medium 206, it can spread to cover a larger area of the surface 207. Thus, with respect to the solution droplet 710B, the droplet 710B covers a particular area of the three-dimensional surface 207 as shown in FIG. 7B, but ultimately spreads to cover a larger area 718 of the surface 207. The spreading margin factor M is equal to the distance 720 plus the radius of the circle 710B. As can be appreciated by those of ordinary skill within the art, M can be a complex function of the number of passes, the solution in question, the temperature of the target, as well as other factors.

Referring back to FIG. 7A, the thickness of the coating 216 can also be controlled by initially preparing the three-dimensional surface 207 of the device medium 206 to ensure that the surface 207 is uniformly wettable in those locations onto which the solution 208 is to be thermally ejected (706). Uniform wettability helps ensure that the coating 216 maintains a desired, uniform thickness in accordance with equation (2). If the three-dimensional surface 207 is not uniformly wettable, or dries in a non-uniform way, then the coating 216 may not have the desired, uniform thickness, but rather have an uneven thickness in places. Wettability may be ensured by initially coating the entire three-dimensional surface 207 with a wettability agent or material, such as polymers (e.g., parylene), silane coupling agents, etchants (e.g., nitric-phosphoric acid), or other surface modification techniques, such as grit blasting and the deposition of other materials via electrolysis. It is noted that the techniques to make a surface non-wettable can also be used to make the surface wettable. For instance, parylene may be wetting with respect to one solvent but non-wetting with respect to another solvent.

Furthermore, the three-dimensional surface 207 may be designed to be selectively non-wettable, such that locations thereof that are not to receive the solution 208, based on the desired pattern 356, are treated with a material that renders them substantially non-wettable. Examples of such a material include polymers (e.g., parylene), silane coupling agents, etchants (e.g., nitric-phosphoric acid), or other surface modification techniques, such as grit blasting and the deposition of other materials via electrolysis. Alternatively, the three-dimensional surface 207 may not be intrinsically uniformly wettable, such that locations thereof that are to receive the solution 208, based on the desired pattern 356, are treated with a material that renders them substantially uniformly wettable, such as polymers (e.g., parylene), silane coupling agents, etchants (e.g., nitric-phosphoric acid), or other surface modification techniques, such as grit blasting and the deposition of other materials via electrolysis, as noted above.

Finally, the thickness of the coating 216 may be controlled by specifying within a predetermined range (708) the Weber value of the droplets of the solution 208 ejected onto the three-dimensional surface 207 of the device medium 206. The Weber value of the solution droplets is the ratio of the kinetic energy of a droplet to the surface energy of the droplet. Droplets having too high of a Weber value "splat" upon contacting the three-dimensional surface 207, in that they undesirably spread more than the spreading margin factor M of equation (2), because these droplets impact the surface 207 with too much kinetic energy. By comparison, droplets having too low of a Weber value can bounce off the three-dimensional surface 207 one or more times before landing on the surface 207 or elsewhere, such that the droplets do not ultimately rest at their intended destination.

In one embodiment, the Weber value for a droplet of the solution 208 may be determined via:

$$We = \frac{D_{sol} R_{drop} V_{droplet}^2}{6T_{sol}} \quad (4)$$

In equation (4), the Weber value We for a solution droplet is specified by the density of the solution $D_{sol}$, multiplied by the radius of the droplet $R_{drop}$, times the square of the velocity at which the droplet impacts the three-dimensional surface $V_{droplet}$, and divided by six times the surface tension of the solution $T_{sol}$. In one embodiment, the Weber value should be within a range of three to thirty, so that the droplets of the solution 208 neither "splat" nor bounce. The Weber value can be controlled, or specified, by adjusting one or more of the parameters of equation (4).

Scaling Desired Pattern Resolution to Fluid-Ejection Resolution

The desired pattern 356 of the coating 216 to be established on the three-dimensional surface 207 of the device medium 206 may have a resolution that is expressed in dots-per-inch (DPI) or pixels-per-inch (PPI). The fluid-ejection nozzles 204 of the fluid-ejection mechanism 202 likewise have a resolution, which may be expressed in DPI or PPI, at which they are capable of ejecting droplets of the solution 208 onto the three-dimensional surface 207. In some situations, the resolution of the desired pattern 356 may be equal to the resolution of the fluid-ejection nozzles 204. However, in other situations, the resolution of the desired pattern 356, which may be referred to as $R_1$, may be greater than the resolution of the fluid-ejection nozzles 204, which may be referred to as $R_2$.

In this latter situation, the pixels of the desired pattern 356 are not easily mapped to pixels ejectable by the fluid-ejection nozzles 204, since $R_1$ is greater than $R_2$. In such a case, a pixel ejectable by the fluid-ejection nozzles 204 maps to $$2^{\frac{R_1}{R_2}}$$

pixels of the desired pattern 356. Therefore, one embodiment of the invention employs a scaling threshold number to determine whether a pixel of the fluid-ejection nozzles 204 is on (i.e., whether a droplet of the solution 208 is to be ejected for the pixel for that pass), or off (i.e., no solution droplets are ejected for the pixel for that pass) for a given corresponding group of $$2^{\frac{R_1}{R_2}}$$

pixels of the desired pattern 356. In particular, if the number of pixels within such a group of pixels of the desired pattern 356 is equal to or greater than the scaling threshold number, than the corresponding pixel of the fluid-ejection nozzles 204 is on, and otherwise the corresponding pixel is off.

Figure 8A:
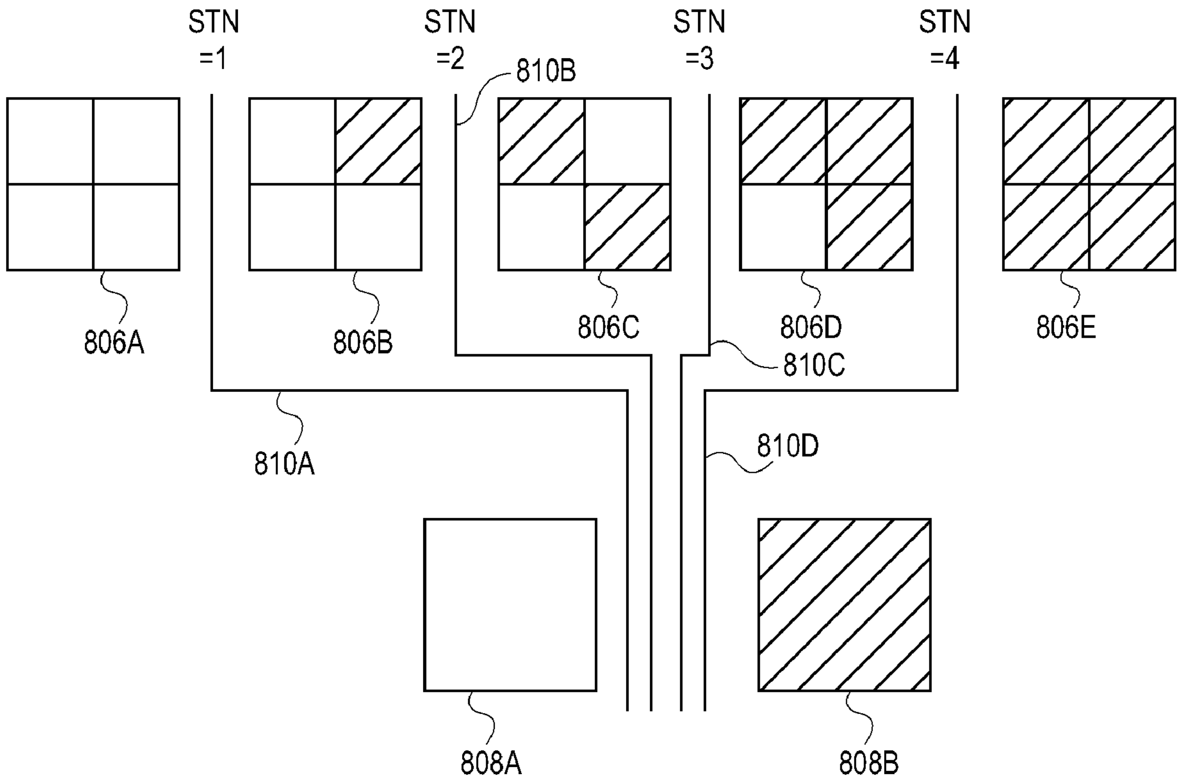
FIG. 8A is a diagram illustratively depicting usage of a scaling threshold number when coating a device medium, according to an embodiment of the invention.

FIG. 8A illustratively depicts representative usage of such a scaling threshold number, according to an embodiment of the invention. In FIG. 8A, the resolution of the desired pattern 356, $R_1$, is 1200 DPI, whereas the resolution of the fluid-ejection nozzles 204, $R_2$, is 600 DPI. Therefore, each pixel of the fluid-ejection nozzles 204 maps to four pixels of the desired pattern 356. For instance, each pixel of the fluid-ejection nozzles 204 can map to a square grid of four pixels of the desired pattern 356. The pixel of the fluid-ejection nozzles 204 can either be off, such that no solution 208 is ejected for the pixel, as in pixel 808A, or the pixel of the nozzles 204 can be on, such that solution 208 is ejected for the pixel, as in pixel 808B.

For any given group of four pixels of the desired pattern 356, there are five different possibilities: no pixels on, as in pixel group 806A; one pixel on, as in pixel group 806B; two pixels on, as in pixel group 806C; three pixels on, as in pixel group 806D; and, all four pixels on, as in pixel group 806E. Which of the pixels of the groups 806B, 806C, and 806D are on and which are off does not matter in one embodiment. For example, in the pixel group 806C, the upper left-hand pixel and the lower right-hand pixel are on, and the other two pixels are off. However, the pixel group 806C also represents and exemplifies the scenario where the top two pixels are on and the bottom two pixels are off (or vice-versa); the left two pixels are on and the right two pixels are off (or vice-versa); and, the upper right-hand pixel and the lower left-hand pixel are on, and the other two pixels are off.

Four different scaling threshold numbers 1, 2, 3, and 4, are represented in FIG. 8A by the lines 810A, 810B, 810C, and 810D. The scaling threshold number of 1, represented by the line 810A, means that at least one pixel of any of the pixel groups 806 has to be on for the corresponding pixel of the fluid-ejection nozzles 204 to be on. Thus, in relation to the scaling threshold number of 1, the pixel group 806A does not correspond to the on pixel 808B of the fluid-ejection nozzles 204, but rather corresponds to the off pixel 808A. By comparison, in relation to the scaling threshold number of 1, the pixel groups 806B, 806C, 806D, and 806E all correspond to the on pixel 808B, since they each have at least one "on" pixel in their two-by-two image pixel.

The scaling threshold numbers of 2, 3, and 4, represented by the lines 810A, 810B, and 810C, means that at least two, three, or four pixels, respectively, of any of the pixel groups 806 have to be on for the corresponding pixel of the fluid-ejection nozzles 204 to be on. For example, in relation to the scaling threshold number of 3, the pixel groups 806A, 806B, and 806C correspond to the off pixel 808A, because they have just zero, one, and two constituent pixels on, respectively. By comparison, in relation to the scaling threshold number of 3, the pixel groups 806D and 806E both correspond to the on jetting pixel 808B, since they each have at least three image pixels on.

In different embodiments of the invention, different scaling thresholds can be selected. For example, if a more-saturated pattern 356 is desired to be coated on the device medium 206, a lower scaling threshold number is selected, because less pixels of any given group of pixels of the pattern 356 have to be on for the corresponding pixel of the fluid-ejection nozzles 204 to be on. By comparison, if a less-saturated pattern 356 is desired to be coated on the device medium 206, a higher scaling threshold number is selected, because more pixels of any given group of pixels of the pattern 356 have to be on for the corresponding pixel of the fluid-ejection nozzles 204 to be on.

Figure 8B:
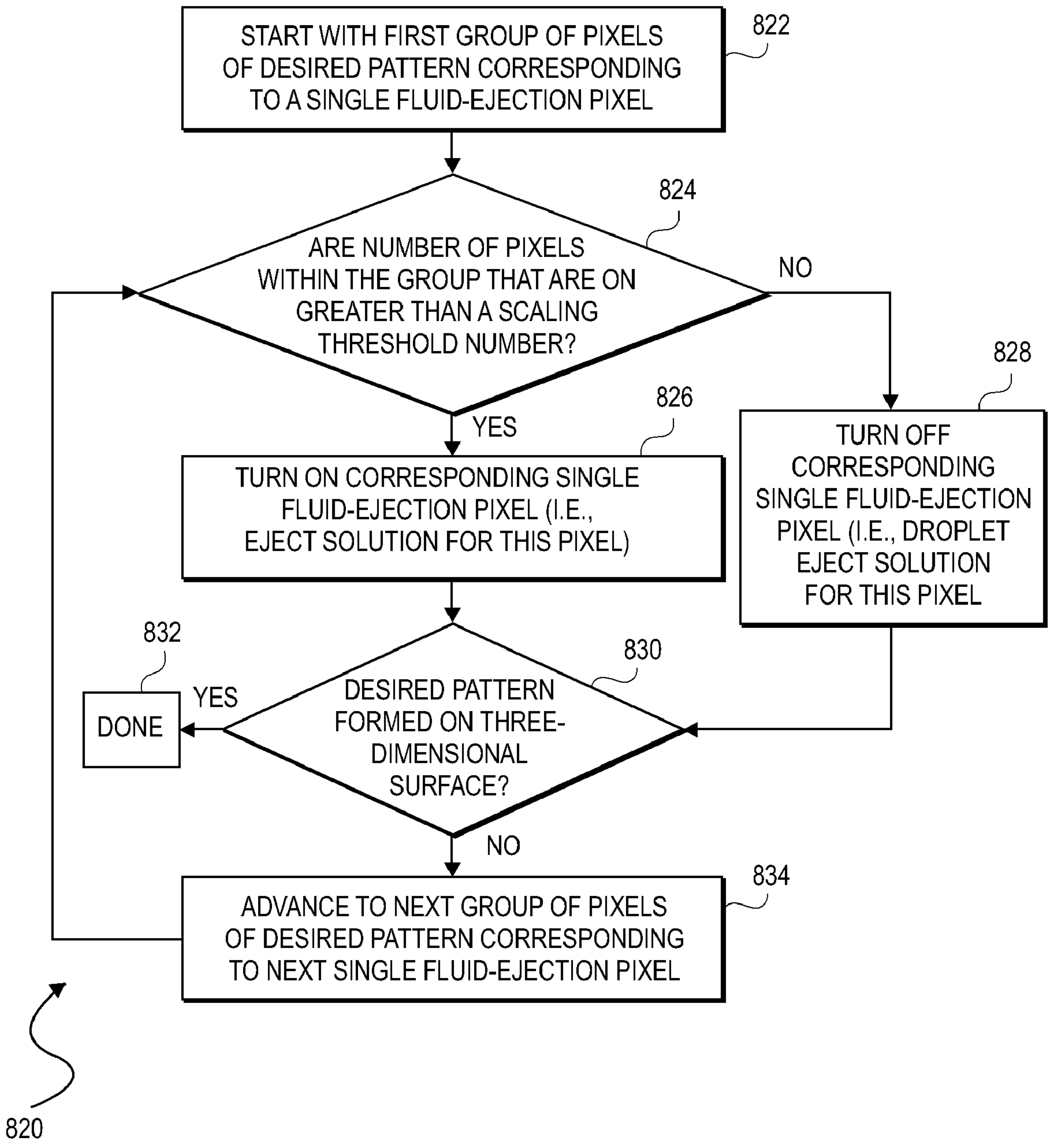
FIG. 8B is a flowchart of a method that uses a predetermined scaling threshold number to scale a larger resolution of a desired pattern to a smaller resolution of fluid-ejection nozzles of a thermal fluid-ejection mechanism, according to an embodiment of the invention.

FIG. 8B shows a method 820 that employs a predetermined scaling threshold number to scale a larger resolution $R_1$ of the desired pattern 356 to a smaller resolution $R_2$ of the fluid-ejection nozzles 204 of the fluid-ejection mechanism 202, according to an embodiment of the invention. The method 820 may be performed as part of part 108 of the method 100 of FIG. 1. In general, each fluid-ejection pixel corresponds to a group of $$2^{\frac{R_1}{R_2}}$$

pattern pixels of the desired pattern 356. The pattern pixels of the desired pattern 356 are therefore divided into groups, and the method 820 is performed in relation to these groups of pixels.

The method 820 starts with the first group of pixels of the desired pattern 356 as corresponding to a single fluid-ejection pixel (822). If the number of pixels within this group of pattern pixels is greater than the scaling threshold number (824), then the corresponding single fluid-ejection pixel is turned on (826). That is, the solution 208 is ejected by the fluid-ejection nozzles 204 for this pixel. Otherwise (824), the corresponding single-fluid ejection pixel is turned off (828), such that none of the solution 208 is ejected by the fluid-ejection nozzles 204 for this pixel.

In either case, if the desired pattern 356 has been completely formed on the three-dimensional surface 207 of the device medium 206 (830), such that all of the groups of pixels of the pattern 356 have been evaluated in part 824, then the method 820 is finished (832). Otherwise, the method 820 advances to the next group of pixels within the desired pattern 356, corresponding to the next single fluid-ejection pixel (834). The method 820 then repeats at part 824 with respect to this group of pixels.

Satisfaction of Flux Constraint

When applying the coating 216 to the three-dimensional surface 207 of the device medium 206, there is a flux limit past which an acceptable coating cannot be established for topography or "drippage" reasons. That is, the flux limit relates to the overall rate at which the solution can be applied to the three-dimensional surface 207, considering both the solution per time per area on a given pass and the time between passes of the fluid-ejection mechanism 202 over this location before the coating 216 becomes unacceptable, from the standpoint of coating uniformity or spreading. Unacceptability may mean that the coating 216 is too rough or coarse, too widely spread, or has some other undesired topography. The flux limit itself is thus the number of times a given location on the three-dimensional surface 207 can receive the solution 208 during successive passes of the fluid-ejection mechanism 202 thereover before the resultant coating 216 becomes too rough or coarse, too widely spread, or otherwise has an undesired topography in relation to the desired pattern 356.

Figures 9A, 9B:
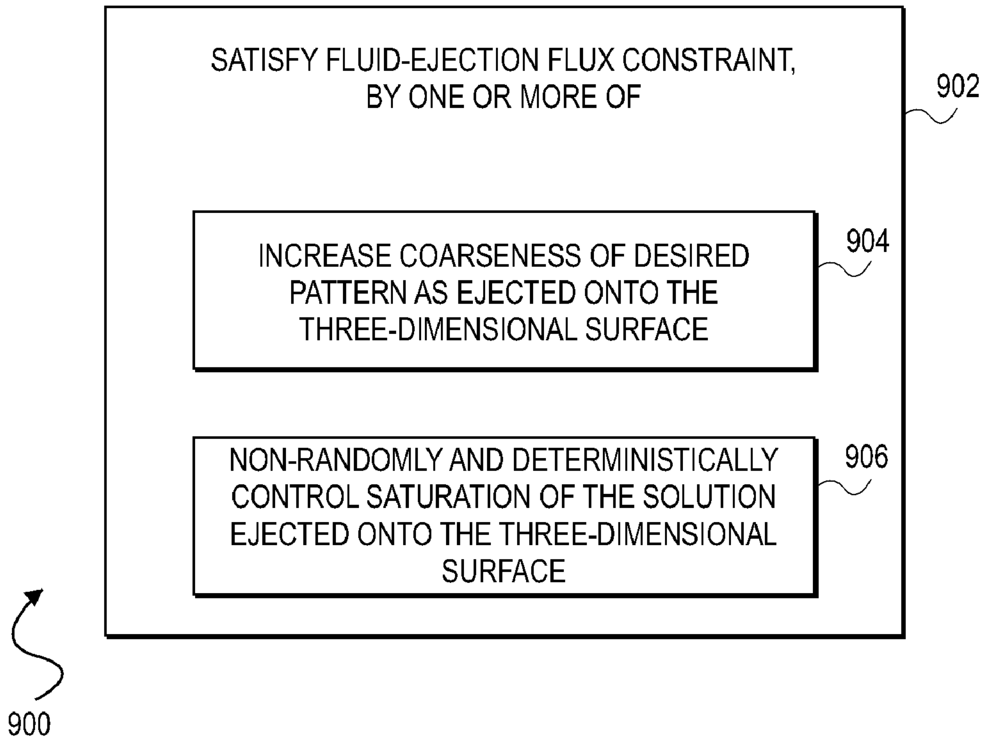
FIG. 9A is a flowchart of a method for satisfying a flux constraint, or limit, when coating a device medium, according to an embodiment of the invention.
FIG. 9B is a diagram of a table for a representative non-random and deterministic saturation control approach for different saturation levels, according to an embodiment of the invention.

FIG. 9A shows a method 900 for satisfying this fluid-ejection flux constraint, according to one embodiment of the invention. The method 900 may be performed as part of part 108 of the method 100 of FIG. 1. The method 900 satisfies the fluid-ejection flux constraint (902) by performing part 904 and/or part 906. Each of these parts 904 and 906 is now described in detail.

First, the coarseness of the desired pattern 356, as ejected by the fluid-ejection nozzles 204 onto the three-dimensional surface 207, may itself simply be increased (904). That is, the flux constraint, or limit, specifies the overall solution mass per unit time per unit area (or per pixel), considering both the material deposited per pass and the time between passes, before the resultant coating 216 becomes too rough or coarse, or too widely spread, in relation to the desired pattern 356. Therefore, if the desired pattern 356 is itself made rougher or coarser or more widely spread even if ejection of the solution 208 results in a rough coating 216, the flux constraint is satisfied in relation to the desired pattern 356, because the dictates of the pattern 356 are relaxed in relation to roughness, coarseness or spreading Second, the saturation of the solution 208 as fluidically ejected onto the three-dimensional surface 207 may be non-randomly and deterministically controlled to satisfy the flux constraint (906). Saturation refers to the percentage of fluid-ejection pixels which are executed/ejected in a given pass, or the number of times a given location on the three-dimensional surface 207 is to maximally receive the solution 208 during successive passes of the fluid-ejection mechanism 202 thereover, divided by the total number of passes. For example, if a given location is passed over by the fluid-ejection mechanism 202 eight times, 50% saturation means that at most the location can receive the solution 208 four of these times. As another example, if a given location is passed over eight times, 25% saturation means that at most the location can receive the solution is two of these times.

The saturation is non-random and deterministic in that in which of the passes of the fluid-ejection mechanism 202 over a given location on the three-dimensional surface 207 the surface 207 receives the solution 208 is non-randomly and deterministically controlled. For example, if the fluid-ejection mechanism 202 passes over a given location eight times at 50% saturation, then the location receives the solution 208 four of these times, but which of the four passes the location receives the solution 208 is not dictated by the saturation setting of 50% itself. A random and non-deterministic saturation is ill suited to satisfy the flux constraint on a pixel basis or length-scale, and even apart from that may not cover the part uniformly when a small number of passes is involved.

Therefore, embodiments of the invention instead employ a non-random and deterministic approach to achieve a given saturation. In one embodiment, a regular approach is employed, such that a regular pattern of solution ejection is achieved to satisfy a given saturation. For example, for 50% saturation, every other pass of the fluid-ejection mechanism 202 may result in the solution 208 being ejected onto a given location of the three-dimensional surface 207. This pattern of eject solution-do not eject solution-eject solution-do not eject solution is a regular pattern, and thus a non-random and deterministic approach to saturation control. As another example, for 25% saturation, every fourth pass of the fluid-ejection mechanism 202 may result in the solution 208 being ejected onto a given location of the three-dimensional surface 207.

Thus, to satisfy a flux constraint, the number of times M that the solution 208 is actually ejected onto a given location of the three-dimensional surface 207 within a number of successive passes N that the fluid-ejection mechanism 202 is scanned over the location is decreased, such that $M \leqq N$. Stated another way, the saturation of any location on the three-dimensional surface 207 can be reduced to satisfy the flux constraint. If the saturation is initially at 100%, for instance, and if the flux constraint is not satisfied, then the saturation may be reduced to 75%, 50%, 25%, and so on, until the flux constraint becomes satisfied.

FIG. 9B shows a table 920 of a non-random and deterministic approach to achieve 100%, 50%, and 25% saturation for a given location, or pixel, of the three-dimensional surface 207 of the device medium 206 where the fluid-ejection mechanism 202 passes four times over the given location, according to an embodiment of the invention. For 100% saturation, the fluid-ejection mechanism 202 ejects the solution 208 onto the location during each of its four passes over the location. For 50% saturation, the mechanism 202 ejects the solution 208 just during the first and the third passes over the location. For 25% saturation, the mechanism 202 ejects the solution 208 just during the first pass.

The table 920 is thus followed each time any location on the three-dimensional surface 207 is to receive the solution 208, for a given saturation. For example, for 50% saturation, a given location may always receive the solution 208 on the first and third passes, and may never receive the solution 208 on the second and fourth passes. This is why this approach to 50% saturation is deterministic and non-random; there is no chance, using the approach of the table 920, that a given location, at 50% saturation, will ever receive the solution on the second or fourth pass.

Coating Control Parameters

The thickness of the coating 216 on the three-dimensional surface 207 of the device medium 206—that is, the thickness of the solute 212 thereon after the solvent 512 has evaporated—can be controlled as has been described in a preceding section of the detailed description. Furthermore, however, the uniformity of the thickness of the coating 216 can be optimized so that it does not undesirably vary. Optimizing thickness uniformity in turn optimizes edge sharpness of the desired pattern 356 as fluidically realized on the three-dimensional surface 207. That is, edges within the desired pattern 356 are desirably and optimally as sharp upon the realization of the pattern 356 on the three-dimensional surface 207 as they are when the pattern 356 is first abstractly generated.

Figure 10:
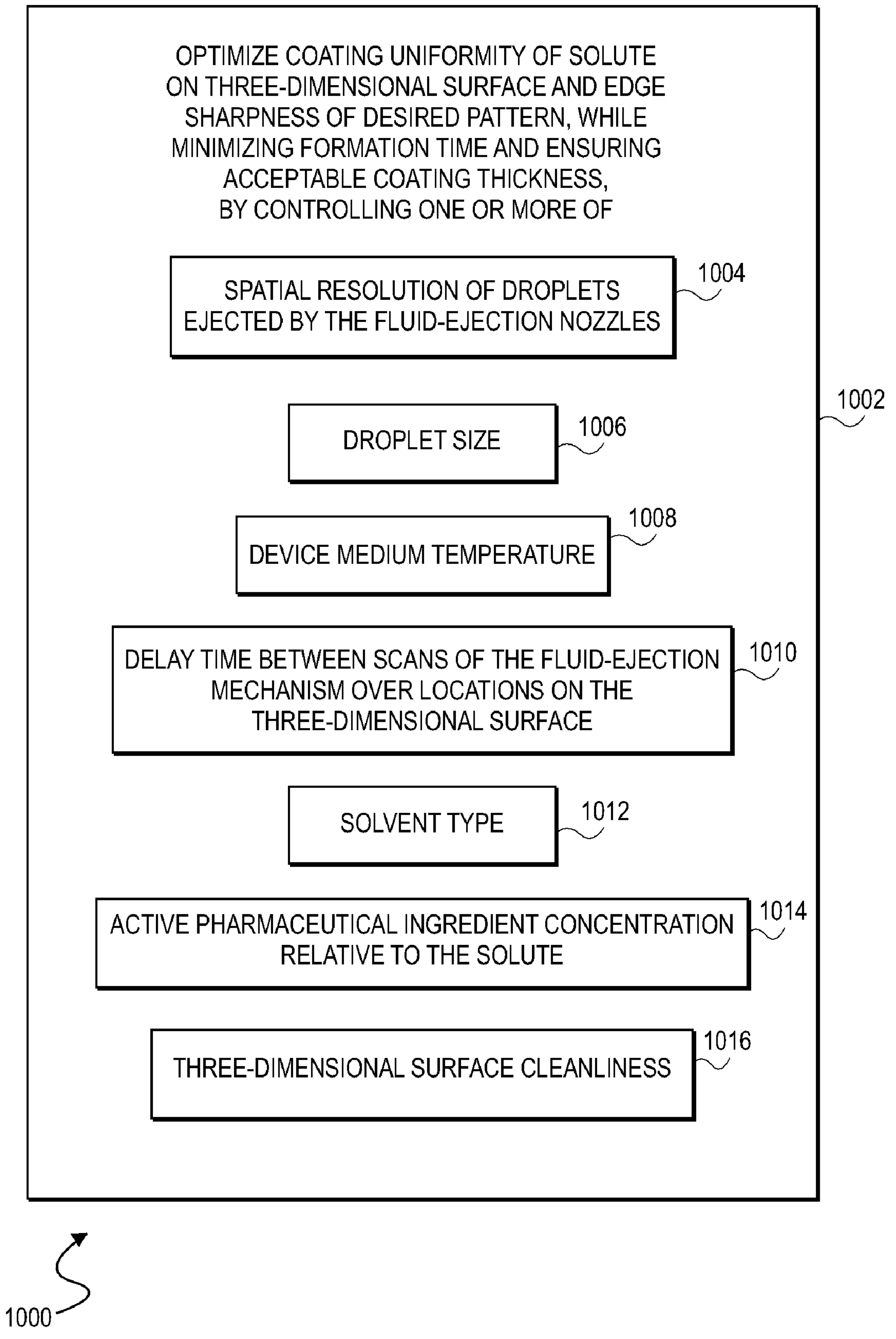
FIG. 10 is a flowchart of a method for optimizing the thickness and the pattern edge sharpness of a coating 216 on a three-dimensional surface of a device medium, according to an embodiment of the invention.

FIG. 10 shows a method 1000 for optimizing the thickness and the pattern edge sharpness of the coating 216 on the three-dimensional surface 207 of the device medium 206, according to an embodiment of the invention. The method 1000 may be performed as part of part 108 of the method 100 of FIG. 1. The method 1000 performs this optimization by controlling one or more of the parameters 1004, 1006, 1008, 1010, 1012, 1014, and 1016 (1002). Each of these parameters is now described in more detail.

The first parameter 1004 is the spatial resolution of the droplets ejected by the fluid-ejection nozzles 204 of the fluid-ejection mechanism 202. The spatial resolution of a droplet of the solution 208 is the distance along the x-axis and the distance along the y-axis that the solution droplet extends over when impacting the three-dimensional surface 207, before the droplet spreads, as has been described in relation to FIG. 7B. If a flux limit is being exceeded, decreasing the spatial resolution of the droplets will tend to improve thickness uniformity and pattern edge sharpness.

The second parameter 1006 is droplet size of the droplets ejected by the fluid-ejection nozzles 204 of the fluid-ejection mechanism 202, which is related to the first parameter 1004. The droplet size, such as the droplet volume, also contributes to thickness uniformity and pattern edge sharpness. In general, the smaller the droplet size, the greater the thickness uniformity and pattern edge sharpness.

The third parameter 1008 is the temperature of the device medium 206 while the three-dimensional surface 207 thereof receives the solution 208. The temperature is desirably within a nominal range, such as between 22 and 40 degrees Celsius (° C.). If the device medium temperature is too hot, the solution 208 may not properly spread, negatively affecting coating thickness uniformity. Likewise, if the device medium temperature is too cold, the solution 208 may spread too much, which also negatively affects coating thickness uniformity.

The fourth parameter 1010 is the delay time between scans, or passes, of the fluid-ejection mechanism 202 over locations on the three-dimensional surface 207. For example, as has been described in relation to FIG. 4B, the fluid-ejection mechanism 202 may pass over a current swath of the three-dimensional surface 207 one or more times before advancing to the next swath of the surface 207 and repeating this process. The delay time between passes, or scans, over a given swath of the three-dimensional surface 207 can be adjusted to optimize coating uniformity and pattern edge sharpness. The optimal delay time may be experimentally determined. In general, too short of a delay time may result in the flux constraint, as has been described above, being exceeded, whereas too long of a delay time may result in undesirably slow throughput and/or the nozzle decap issues described previously.

The fifth parameter 1012 is the type of the solvent 512 that is used within the solution 208. Different types of solvents, for instance, have different vapor pressures and resultant rates of evaporation, as well as other different physical properties. With respect to evaporation rate, a solvent having a faster rate may require less delay time between scans—meaning it has a higher flux limit) as compared to a solvent having a slower rate—to achieve the same coating thickness uniformity and pattern edge sharpness optimization.

The sixth parameter 1014 is the concentration of the solute (i.e., the active pharmaceutical ingredient plus the polymer) in the solution. Driving this concentration as high as possible is of value in putting less solvent on the part for a given mass of solute to be delivered; this helps the process stay within its flux limit and increases throughput; reliable jetting and decap behavior end up being the constraint on how high one can take this concentration. Two related parameters include the specific concentration of the polymer, and the specific concentration of the active pharmaceutical ingredient.

Finally, the seventh parameter is the cleanliness of the three-dimensional surface 207 of the device medium 206 (1016). The cleaner the three-dimensional surface 207 is, the easier it generally is to optimize coating thickness uniformity and pattern edge sharpness. Likewise, the less clean the three-dimensional surface 207 is, the more difficult it generally is to optimizing coating thickness uniformity and pattern edge sharpness.

Coating Surface Roughness

Besides controlling the thickness of the coating 216 on the three-dimensional surface 207 of the device medium 206, and the uniformity of this thickness, the surface roughness of the coating 216 on the surface 207 can be controlled. In some applications, a rougher surface of the coating 216 on the three-dimensional surface 207 of the device medium 206 may be desired. In other applications, a smoother surface may be desired. In general, the fewer passes of the fluid-ejection mechanism 202 over the three-dimensional surface 207, where the mechanism 202 ejects fluid over each of these passes, and with more of the solution 208 deposited in each pass, the greater the surface roughness, as compared to having more passes with less of the solution 208 deposited in each pass.

Figure 11:
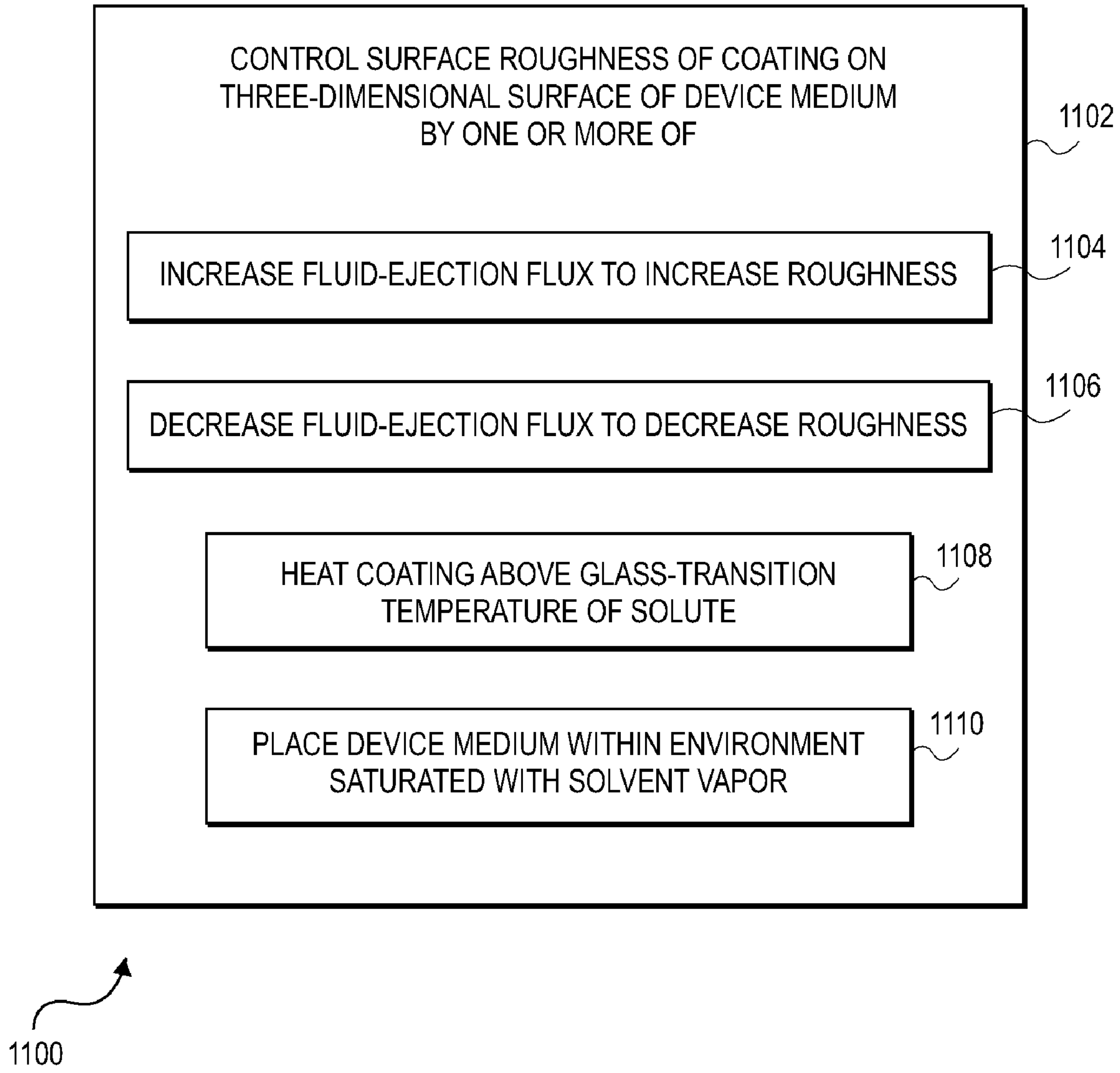
FIG. 11 is a flowchart of a method for controlling surface roughness of a coating on a three-dimensional surface of a device medium, according to an embodiment of the invention.

FIG. 11 shows a method 1100 for controlling surface roughness of the coating 216 on the three-dimensional surface 207 of the device medium 206 in a number of other ways, according to an embodiment of the invention. The method 1100 may be performed as part of part 108 of the method 100 of FIG. 1. The method 1100 controls surface roughness of the coating 216 (1102) by performing one or more of parts 1104, 1106, 1108, and 1110. Each of these parts is now described in more detail.

Increasing the fluid-ejection flux increases surface roughness of the coating 216 on the three-dimensional surface 207 (1104), whereas decreasing the flux decreases surface roughness of the coating 216 (1106). Flux refers to the volume of liquid dispensed over a given period of time per unit area. Use of a lower fluid-ejection, or dispense, flux when ejecting the solution 208 from the fluid-ejection nozzles 204 onto the three-dimensional surface 207 generally allows the resultant layer to dry more quickly, before migration of the solute 212 can occur, leading to a smoother surface of the coating 216. Likewise, utilization of a higher fluid-ejection, or dispense, flux when ejecting the solution 208 onto the surface 207 generally means that the resultant layer dries more slowly, such that migration of the solute 212 is more likely to occur, leading to a rougher and less well confined surface of the coating 216.

Once the coating 216 has been established on the three-dimensional surface 207—that is, after evaporation of the solvent 510 from the deposited solution 208 on the surface 207—the coating 206 may be heated above the glass-transition temperature of the solute 212 to reduce surface roughness (1108). The glass-transition temperature of the solute 212 is the temperature at which the solute 212 becomes a glass. This is why heating the coating 216 past this temperature results in the coating 216 becoming less rough.

Furthermore, placing the device medium 206, before the solvent 510 has completely evaporated, within an environment that is saturated with vapor of the solvent 510 can reduce surface roughness (1110). Such placement reduces the rate of evaporation of the solvent 510. Reducing the evaporative rate of the solvent 510 reduces surface roughness, because the resultant coating 216 is permitted to dry in a more orderly and controlled fashion.

Layer-by-Layer and Intra-Layer Thickness and Composition Control

Figure 12A:
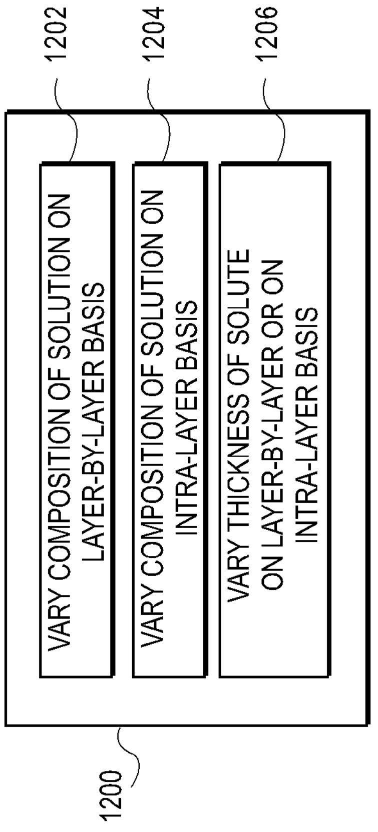
FIG. 12A is a flowchart of a method of how a coating on a three-dimensional surface of a device medium can be varied in different ways, according to an embodiment of the invention.

FIG. 12A shows a method 1200 of how the coating 216 can be varied in different ways, according to an embodiment of the invention. The method 1200 can be performed as part of part 108 of the method 100 in one embodiment. The method 1200 includes performing one or more of parts 1202, 1204, and 1206. Each of these parts is now described in more detail.

On a layer-by-layer basis, the composition of the solution 208 may be varied in relation to the three-dimensional surface 207 of the device medium 206 (1202). For instance, for a first pass over the three-dimensional surface 207, the solution 208 may include at least a particular type of the polymer, a particular type of the active pharmaceutical ingredient 214, a particular concentration of the active pharmaceutical ingredient 214 within the polymer, and a particular concentration of the polymer within the solvent 510. For a second pass over the three-dimensional surface 207, the composition of the solution 208 may vary insofar as the solute type, the active pharmaceutical ingredient type, the solvent type, and/or the concentration of the active pharmaceutical ingredient within the solute may be varied.

In addition, on an intra-layer basis, the composition of the solution 208 may be varied in relation to the three-dimensional surface 207 of the device medium 206 (1204). For example, during a given pass over the three-dimensional surface 207, the concentration of the active pharmaceutical ingredient 214 within the polymer may not be homogeneous. Rather, there may be localized greater concentrations of the ingredient 214 within the solute 212, as well as localized lesser concentrations of the ingredient 214 within the solute 212. As a result, during dispensing of the solution 208 onto the three-dimensional surface 207 to realize a given, single layer of the coating 216, some locations of the surface 207 may receive solution 208 that has greater concentrations of the active pharmaceutical ingredient 214 within the polymer 212, and other locations may receive solution 208 that has lesser concentrations of the ingredient 214 within the solute 212.

Finally, on either an inter-layer basis (i.e., a layer-by-layer basis) or on an intra-layer basis, the thickness of the solute 212 of the resultant coating 216 may be varied (1206). For example, some layers, corresponding to the different number of passes over the three-dimensional surface 207 by the fluid-ejection mechanism 202, may be thinner or thicker than other layers. Furthermore during dispensing of the solution 208 during a given pass, more of the solution 208 may be ejected onto the surface 207 in some locations than in other locations, such that a given layer may purposefully not have uniform thickness.

Figure 12B:
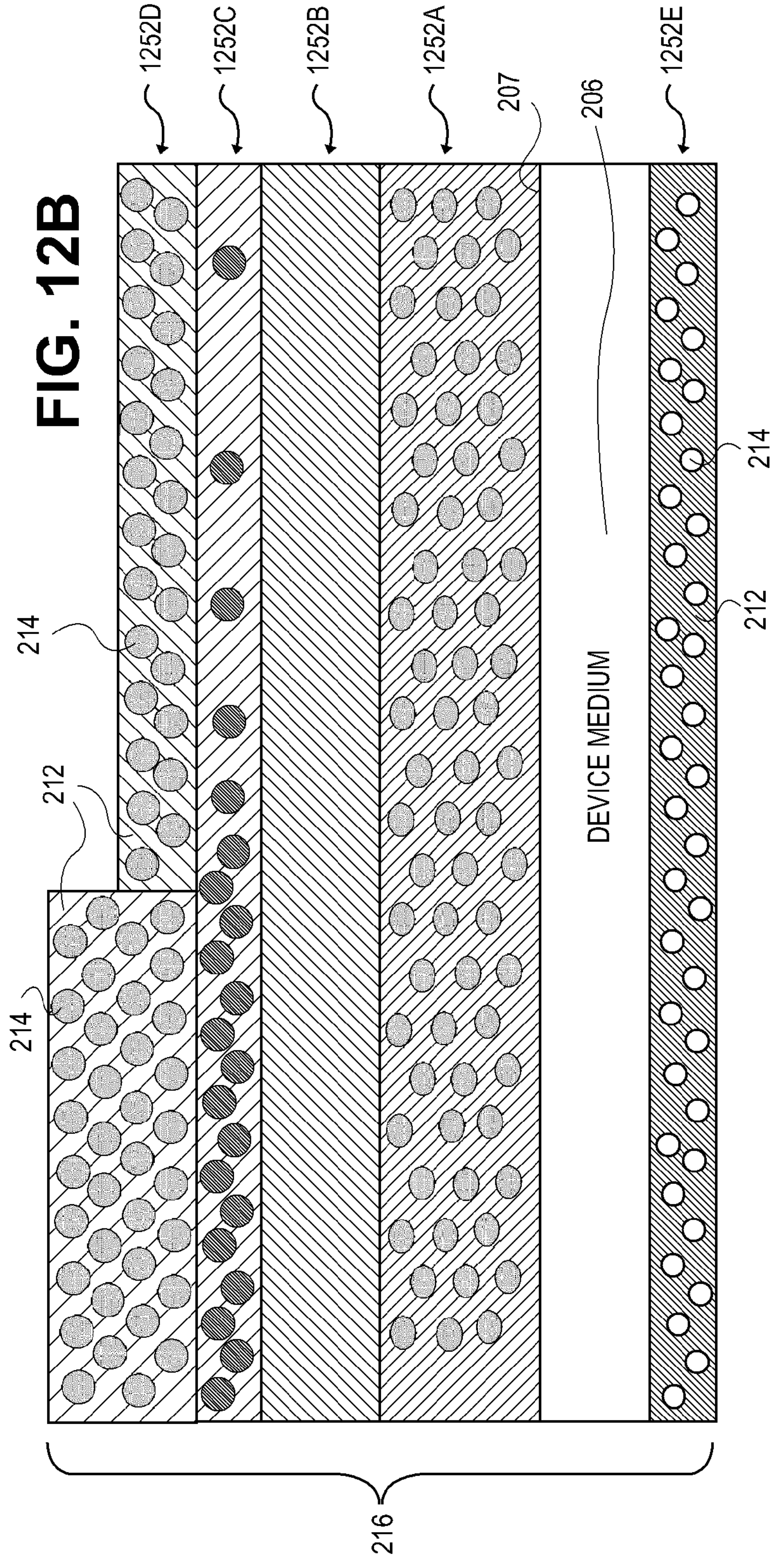
FIG. 12B is a diagram depicting how a coating on a three-dimensional surface of a device medium can vary in different ways, according to an embodiment of the invention.

FIG. 12B shows illustrative performance of the method 1200, according to an embodiment of the invention. The device medium 206 has a coating 216 that includes layers 1252A, 1252B, 1252C, 1252D, and 1252E, collectively referred to as the layers 1252. The layers 1252A, 1252B, 1252C, and 1252D are located on the three-dimensional (exterior) surface of the device medium 206, whereas the layer 1252E is located on the opposite, interior surface of the medium 206. Within each of the layers 1252, there is polymer (or monomer) 212 within which active pharmaceutical ingredients 214 (depicted as circles) are concentrated, although this is particularly called out in FIG. 12B just in relation to the layers 1252D and 1252E for illustrative clarity.

The different shapes of the active pharmaceutical ingredients or bioactive substances 214 within the layers 1252 denote different active pharmaceutical ingredients 214. Likewise, the different shadings of the polymer within the layers 1252 denote different types of the polymer. As such, the composition of the layers 1252 is varied on a layer-by-layer basis. In addition, the layer 1252B does not have any active pharmaceutical ingredient 214 therein, and thus includes just the polymer. Furthermore, the composition of the layer 1252C in particular varies on an intra-layer basis, insofar as the concentration of the active pharmaceutical ingredient 214 within the polymer 212 decreases from left to right. Finally, the layers 1252 have different thicknesses, and the layer 1252D is thicker to the left than it is to the right.

Topographical Coating Control

Figure 13:
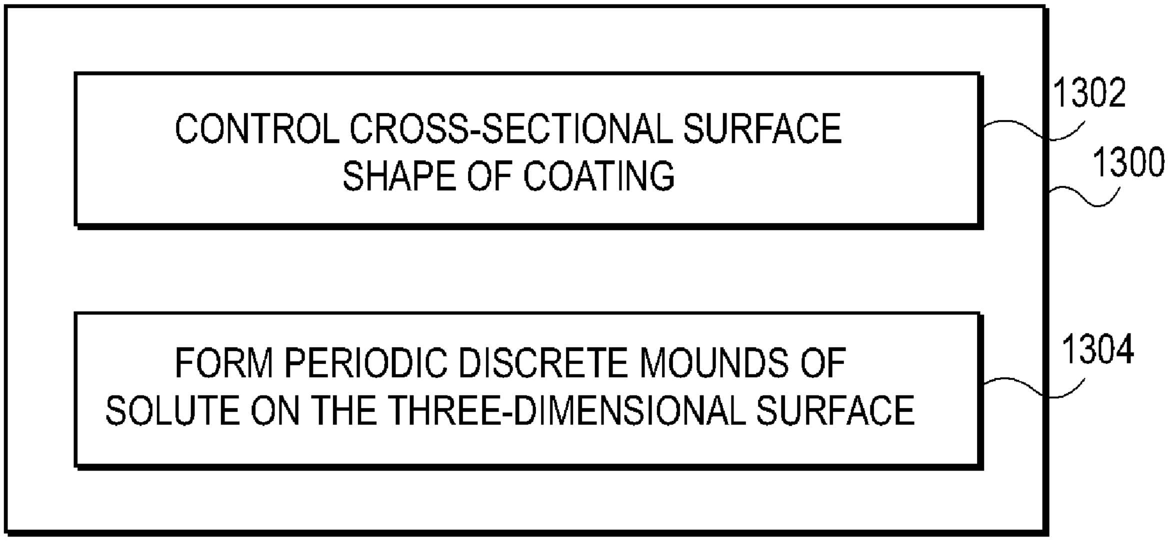
FIG. 13 is a flowchart of a method for varying the topography of a coating on a three-dimensional surface of a device medium, according to an embodiment of the invention.

Finally, besides thickness and composition, the topography of the layers of the coating 216 on the three-dimensional surface 207 of the device medium 206 can also be varied, among other characteristics of the coating 216. FIG. 13 shows a method 1300 for varying the topography of the coating 216 in two different ways, according to an embodiment of the invention. The method 1300 may be performed as part of part 108 of the method 100 in one embodiment. The method 1300 includes performing part 1302 and/or part 1304, each of which is now described in more detail.

First, the cross-sectional surface shape of the coating 216 on the three-dimensional surface 207 may be controlled (1302). For example, grooves within the coating 216 can be formed by varying the dispense, or fluid-ejection, flux of the solution 208 in a particular way. More specifically, where the dispense flux exceeds the flux corresponding to a smooth, flat surface, it has been found that such grooves are created within the resultant coating 216. Such grooves or craters can result from various fluidic evaporation effects. Other types of topographies may also be generated in this manner.

Second, periodic and discrete modules of the solute 212 may be purposefully formed as the coating 216 on the three-dimensional surface 207 (1304). That is, instead of a continuous layer of the coating 216 resulting from continuous ejection or dispensation of the solution 208 from the fluid-ejection nozzles 204 of the fluid-ejection mechanism 202, the solute 212 may instead mound periodically within the resultant coating 216. This effect occurs by leveraging the Rayleigh instability of the solution 208 as the solution 208 is continuously ejected onto the three-dimensional surface. The Rayleigh instability is the surface tension-driven instability of the thin film of the liquid solution 208 that lines a cylindrical surface in particular. For thinly dispensed layers of the solution 208, the periodic mounds form approximately with spacing every $\pi$D to 4.5 D along the length of the device medium 206, where D is the diameter of the medium 206 and where the medium 206 is cylindrically shaped.

We claim:

1. A method comprising:

providing a solution comprising a non-aqueous organic solvent within which a solute has been dissolved;

providing a thermal fluid-ejection mechanism having a plurality of fluid-ejection nozzles and capable of thermally ejecting the solution;

providing a device medium having a three-dimensional surface on which the solution is to be ejected, the device medium being a device having an active functionality performable without assistance from other devices, the three-dimensional surface being a non-planar surface, the three-dimensional surface being three-dimensional on a non-atomic level visible to a human eye; and, controlling the fluid-ejection nozzles of the thermal fluid-ejection mechanism to eject the solution onto the three-dimensional surface of the device medium in accordance with a desired pattern wherein controlling the fluid-ejection nozzles of the thermal fluid-ejection mechanism to eject the solution onto the three-dimensional surface of the device medium comprises one of:

a) substantially ensuring that the solution does not plug any of the fluid-ejection nozzles while the fluid-ejection nozzles are being controlled to eject the solution, by specifying that a Reynolds Number value of the fluid-ejection nozzles in relation to the solution times a Euler Number value of the fluid-ejection nozzles in relation to the solution is greater than a predetermined threshold product of at least ten;

b) controlling a thickness of the solute on the three-dimensional surface of the device medium, as ejected as part of the solution by the fluid-ejection nozzles of the thermal fluid-ejection mechanism, by specifying the thickness in accordance with $$t = \frac{N_{pass} c V_{drop} (N_{nozz} - 1)}{\rho \Delta \times [(N_{nozz} - 1)\Delta y + 2M]},$$

where t is the thickness of the solute, $N_{pass}$ is a number of passes of the thermal fluid-ejection mechanism over the three-dimensional surface, c is concentration of the solute within the solvent, $V_{drop}$ is a volume of a droplet ejected by a fluid-ejection nozzle, $N_{nozz}$ is a number of the fluid-ejection nozzles actively ejecting the solution onto the three-dimensional surface, ρ is a density of the solute on the three-dimensional surface after evaporation of the solvent, Δx and Δy together are spatial resolutions of the droplets ejected along dimensions x and y, and M is a spreading margin factor; and c) scaling a larger resolution $R_1$ of the desired pattern to a smaller resolution $R_2$ of the fluid-ejection nozzles of the thermal fluid-ejection mechanism, based on a scaling threshold number, where each fluid-ejection pixel of a plurality of fluid-ejection pixels ejectable by the fluid-ejection nozzles maps to a group of $$2^{\frac{R_1}{R_2}}$$

pattern pixels of the desired pattern, such that where a number of the group of pattern pixels that are on is equal to or greater than the scaling threshold number, the fluid-ejection pixel is on, and where the number of the group of pattern pixels that are on is less than the scaling threshold number, the fluid-ejection pixel is off, where a given pixel is on, the given pixel is to be printed, and where the given pixel is off, the given pixel is not to be printed.

2. The method of claim 1, wherein the solute comprises one or more of a large molecular weight polymer having a molecular weight of at least fifty thousand atomic mass units (AMU's);

a monomer capable of being converted to a fully formed polymer;

a bioactive substance.

3. The method of claim 1, wherein the fluid-ejection nozzles of the thermal fluid-ejection mechanism are each at least thirty microns in diameter.

4. The method of claim 1, wherein controlling the fluid-ejection nozzles of the thermal fluid-ejection mechanism to eject the solution onto the three-dimensional surface of the device medium further comprises:

moving the thermal fluid-ejection mechanism one or more times in a two-dimensional path corresponding to the desired pattern, over the three-dimensional surface, in a vector mode of operation; and, while the thermal fluid-ejection mechanism is being moved in the two-dimensional path corresponding to the desired pattern, causing the fluid-ejection nozzles to selectively eject the solution onto the three-dimensional surface of the device medium.

5. The method of claim 1, wherein controlling the fluid-ejection nozzles of the thermal fluid-ejection mechanism to eject the solution onto the three-dimensional surface of the device medium further comprises:

repeating one or more times:

advancing the thermal fluid-ejection mechanism relative to the three-dimensional surface in a first dimension so that the thermal fluid-ejection mechanism is incident to a current swath of the three-dimensional surface;

scanning the thermal fluid-ejection mechanism one or more times along a second dimension over the current swath of the three-dimensional surface, the second dimension parallel to the current swath and perpendicular to the first dimension; and, while the thermal fluid-ejection mechanism is being scanned over the current swath, causing the fluid-ejection nozzles to selectively eject the solution onto the three-dimensional surface of the device medium in accordance with a corresponding swath of the desired pattern, until the solution has been ejected onto the three-dimensional surface of the device medium in accordance with the desired pattern.

6. The method of claim 1, further comprising:

calibrating the fluid-ejection nozzles of the thermal fluid-ejection mechanism in relation to the solution to determine a profile particular to the fluid-ejection nozzles and the solution, wherein the profile specifies a number of fluid-ejection pulses to be sent to a fluid-ejection nozzle to unclog the fluid-ejection nozzle after the solution has plugged the fluid-ejection nozzle, as a function of a length of time at which the fluid-ejection nozzle has remained unused, and wherein controlling the fluid-ejection nozzles of the thermal fluid-ejection mechanism to eject the solution onto the three-dimensional surface of the device medium further comprises:

determining that a fluid-ejection nozzle of the thermal fluid-ejection mechanism has been plugged by the solution such that the fluid-ejection nozzle is incapable of ejecting the solution; and, in response, sending a number of fluid-ejection pulses to the fluid-ejection nozzle, based on the profile, to unclog the fluid-ejection nozzle so that the fluid-ejection nozzle is again able to eject the solution.

7. The method of claim 1, wherein controlling the fluid-ejection nozzles of the thermal fluid-ejection mechanism to eject the solution onto the three-dimensional surface of the device medium further comprises:

accelerating evaporation of the solvent from the three-dimensional surface after the solution has been ejected onto the three-dimensional surface, by directly conductively, radiatively, and/or convectively heating the device medium.

8. The method of claim 1, wherein controlling the fluid-ejection nozzles of the thermal fluid-ejection mechanism to eject the solution onto the three-dimensional surface of the device medium further comprises:

satisfying a fluid-ejection flux constraint governing whether an acceptable coating of the solute on the three-dimensional surface is possible based on topographical and/or drippage factors, by increasing coarseness of the desired pattern in accordance with which the fluid-ejection nozzles of the thermal fluid-ejection mechanism are ejected onto the three-dimensional surface.

9. The method of claim 1, wherein controlling the fluid-ejection nozzles of the thermal fluid-ejection mechanism to eject the solution onto the three-dimensional surface of the device medium further comprises:

optimizing coating uniformity of the solute on the three-dimensional surface and edge sharpness of the desired pattern on the three-dimensional surface, while minimizing time of formation of the desired pattern on the three-dimensional surface and ensuring an acceptable thickness of the solute on the three-dimensional surface, by controlling one or more of:

spatial resolution of droplets ejected by the fluid-ejection nozzles of the thermal fluid-ejection mechanism;

size of each droplet ejected by the fluid-ejection nozzles;

temperature of the device medium;

delay time between scans of the thermal fluid-ejection mechanism over the three-dimensional surface of the device medium;

type of the solvent;

concentration of a polymer;

concentration of an active pharmaceutical ingredient; and, cleanliness of the three-dimensional surface.

10. The method of claim 1, wherein controlling the fluid-ejection nozzles of the thermal fluid-ejection mechanism to eject the solution onto the three-dimensional surface of the device medium further comprises:

controlling surface roughness of a coating of the solute on the three-dimensional surface of the device medium, by one or more of:

increasing fluid-ejection flux to increase surface roughness;

decreasing the fluid-ejection flux to decrease surface roughness;

heating the coating of the solute on the three-dimensional surface above a glass-transition temperature of the solute; and, placing the device medium within an environment saturated with vapor of the solvent.

11. The method of claim 1, wherein controlling the fluid-ejection nozzles of the thermal fluid-ejection mechanism to eject the solution onto the three-dimensional surface of the device medium further comprises one or more of:

varying composition of the solution on a layer-by-layer basis in relation to the three-dimensional surface of the device medium;

varying the composition of the solution on an intra-layer basis in relation to the three-dimensional surface; and, varying a thickness of the solute on the three-dimensional surface of the device medium, wherein the composition of the solution comprises in sum at least a specific type of the polymer, a specific type and concentration of an active pharmaceutical ingredient, and a concentration of the total solute in the solution.

12. The method of claim 1, wherein controlling the fluid-ejection nozzles of the thermal fluid-ejection mechanism to eject the solution onto the three-dimensional surface of the device medium further comprises:

controlling a cross-sectional surface shape of a coating of the solution on the three-dimensional surface at least by varying fluid-ejection flux.

13. The method of claim 1, wherein controlling the fluid-ejection nozzles of the thermal fluid-ejection mechanism to eject the solution onto the three-dimensional surface of the device medium further comprises:

purposefully forming periodic discrete mounds of the solute on the three-dimensional surface by leveraging Rayleigh instability of the solution as continuously ejected on the three-dimensional surface by the fluid-ejection nozzles of the fluid ejection mechanism.

14. The method of claim 1, wherein controlling the fluid-ejection nozzles of the thermal fluid-ejection mechanism to eject the solution onto the three-dimensional surface of the device medium further comprises:

accelerating evaporation of the solvent from the three-dimensional surface after the solution has been ejected onto the three-dimensional surface, by flowing gas over three-dimensional surface of the device medium.

15. A method comprising:

providing a solution comprising a non-aqueous organic solvent within which a solute has been dissolved;

providing a thermal fluid-ejection mechanism having a plurality of fluid-ejection nozzles and capable of thermally ejecting the solution;

providing a device medium having a three-dimensional surface on which the solution is to be ejected, the device medium being a device having an active functionality performable without assistance from other devices, the three-dimensional surface being a non-planar surface, the three-dimensional surface being three-dimensional on a non-atomic level visible to a human eye; and, controlling the fluid-ejection nozzles of the thermal fluid-ejection mechanism to eject the solution onto the three-dimensional surface of the device medium in accordance with a desired pattern, wherein controlling the fluid-ejection nozzles of the thermal fluid-ejection mechanism to eject the solution onto the three-dimensional surface of the device medium comprises:

accelerating evaporation of the solvent from the three-dimensional surface after the solution has been ejected onto the three-dimensional surface, by where the device medium is substantially cylindrically shaped and hollow and where the device medium is disposed on a mandrel during ejection of the solution onto the three-dimensional surface, directly conductively heating the mandrel, such that the device medium is indirectly conductively heated.

16. A method comprising:

providing a solution comprising a non-aqueous organic solvent within which a solute has been dissolved;

providing a thermal fluid-ejection mechanism having a plurality of fluid-ejection nozzles and capable of thermally ejecting the solution;

providing a device medium having a three-dimensional surface on which the solution is to be ejected, the device medium being a device having an active functionality performable without assistance from other devices, the three-dimensional surface being a non-planar surface, the three-dimensional surface being three-dimensional on a non-atomic level visible to a human eye; and, controlling the fluid-ejection nozzles of the thermal fluid-ejection mechanism to eject the solution onto the three-dimensional surface of the device medium in accordance with a desired pattern, wherein controlling the fluid-ejection nozzles of the thermal fluid-ejection mechanism to eject the solution onto the three-dimensional surface of the device medium comprises:

accelerating evaporation of the solvent from the three-dimensional surface after the solution has been ejected onto the three-dimensional surface, by where the device medium is substantially cylindrically shaped and hollow and where the device medium is disposed on a mandrel during ejection of the solution onto the three-dimensional surface, and where the mandrel is hollow, flowing gas or liquid through the mandrel.

17. The method of claim 1, wherein controlling the fluid-ejection nozzles of the thermal fluid-ejection mechanism to eject the solution onto the three-dimensional surface of the device medium further comprises:

accelerating evaporation of the solvent from the three-dimensional surface after the solution has been ejected onto the three-dimensional surface, by where the device medium is substantially cylindrically shaped and hollow and where the device medium is disposed on a mandrel during ejection of the solution onto the three-dimensional surface, employing the mandrel as a heating element, such that the device medium is directly conductively heated.

* * * * *